United States Patent
Awano et al.

(10) Patent No.: US 8,535,635 B2
(45) Date of Patent: Sep. 17, 2013

(54) METHOD OF MANUFACTURING CARBON CYLINDRICAL STRUCTURES AND BIOPOLYMER DETECTION DEVICE

(75) Inventors: Yuji Awano, Kawasaki (JP); Akio Kawabata, Kawasaki (JP); Shozo Fujita, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1103 days.

(21) Appl. No.: 12/457,726

(22) Filed: Jun. 19, 2009

(65) Prior Publication Data

US 2010/0124529 A1 May 20, 2010

Related U.S. Application Data

(62) Division of application No. 10/303,083, filed on Nov. 25, 2002, now abandoned.

(30) Foreign Application Priority Data

Nov. 26, 2001 (JP) ................. 2001-359661
Dec. 20, 2001 (JP) ................. 2001-387831
Mar. 19, 2002 (JP) ................. 2002-077036

(51) Int. Cl.
*D01F 9/127* (2006.01)

(52) U.S. Cl.
USPC .......... 423/447.3; 423/447.1; 423/447.2; 257/9; 257/E21.049; 257/E29.082; 427/526; 977/734; 977/750; 977/752; 438/503

(58) Field of Classification Search
USPC ....... 423/447.1–447.3, 445 B; 977/742–754, 977/842–848; 257/9, E21.049, E29.082; 427/526; 438/503
See application file for complete search history.

(56) References Cited

U.S. PATENT DOCUMENTS

| | | | |
|---|---|---|---|
| 6,054,277 A | 4/2000 | Furcht et al. | |
| 6,203,814 B1 | 3/2001 | Fisher et al. | |
| 6,207,369 B1 | 3/2001 | Wohlstadter et al. | |
| 6,303,094 B1 * | 10/2001 | Kusunoki et al. | 423/447.1 |
| 6,346,189 B1 * | 2/2002 | Dai et al. | 205/766 |

(Continued)

FOREIGN PATENT DOCUMENTS

WO   WO 98/39250   * 9/1998

OTHER PUBLICATIONS

Coq, et al., Fullerene-based materials as new support media in heterogeneous catalysis by metals, Applied Catalysis A: General 1998; 173: 175-183.*

(Continued)

*Primary Examiner* — Daniel C McCracken
(74) *Attorney, Agent, or Firm* — Westerman Hattori Daniels & Adrian, LLP

(57) ABSTRACT

A method of manufacturing carbon cylindrical structures, as represented by carbon nanotubes, by growing them on a substrate using a chemical vapor deposition (CVD) method, comprising the steps of implanting metal ions to the substrate surface and then growing the carbon cylindrical structures using the metal ions as a catalyst. A method of manufacturing carbon nanotubes comprising a step of using nano-carbon material as seed material for growing carbon nanotubes is also disclosed. A biopolymer detection device comprising vibration inducing part for inducing vibration, binding part capable of resonating with the vibration induced by the vibration inducing part and capable of binding or interacting with a target biopolymer, and detection part for detecting whether or not the binding part have bound or interacted with the target biopolymer, is also disclosed.

25 Claims, 15 Drawing Sheets

(56) References Cited

U.S. PATENT DOCUMENTS

| | | |
|---|---|---|
| 6,403,309 B1 | 6/2002 | Iris et al. |
| 6,445,006 B1 | 9/2002 | Brandes et al. |
| 2001/0031900 A1 | 10/2001 | Margrave et al. |
| 2002/0180306 A1 | 12/2002 | Hunt et al. |

OTHER PUBLICATIONS

Definition of "implant," accessed online at <http://www.merriam-webster.com/dictionary/implanting> on 13 May 13, 2013.*

Baughman et al., "Carbon nanotube actuators", Science, May 21, 1999, vol. 284, pp. 1340-1344.

Craighead, "Nanoelectromechanical systems", Science, Nov. 24, 2000, vol. 290, pp. 1532-1535.

Fritz et al., "Translating biomolecular recognition into nanomechanics", Science, Apr. 14, 2000, vol. 288, pp. 316-318.

Raiteri et al., "Micromechanical cantilever-based biosensors", Sensors and Actuators B, 2001, vol. 79, pp. 115-126.

Wong et al., "Covalently-functionalized single-walled carbone nanotube probe tips for chemical force microscopy," J. Am. Chem. Soc., 1998, vol. 120, p. 8557-8558.

* cited by examiner

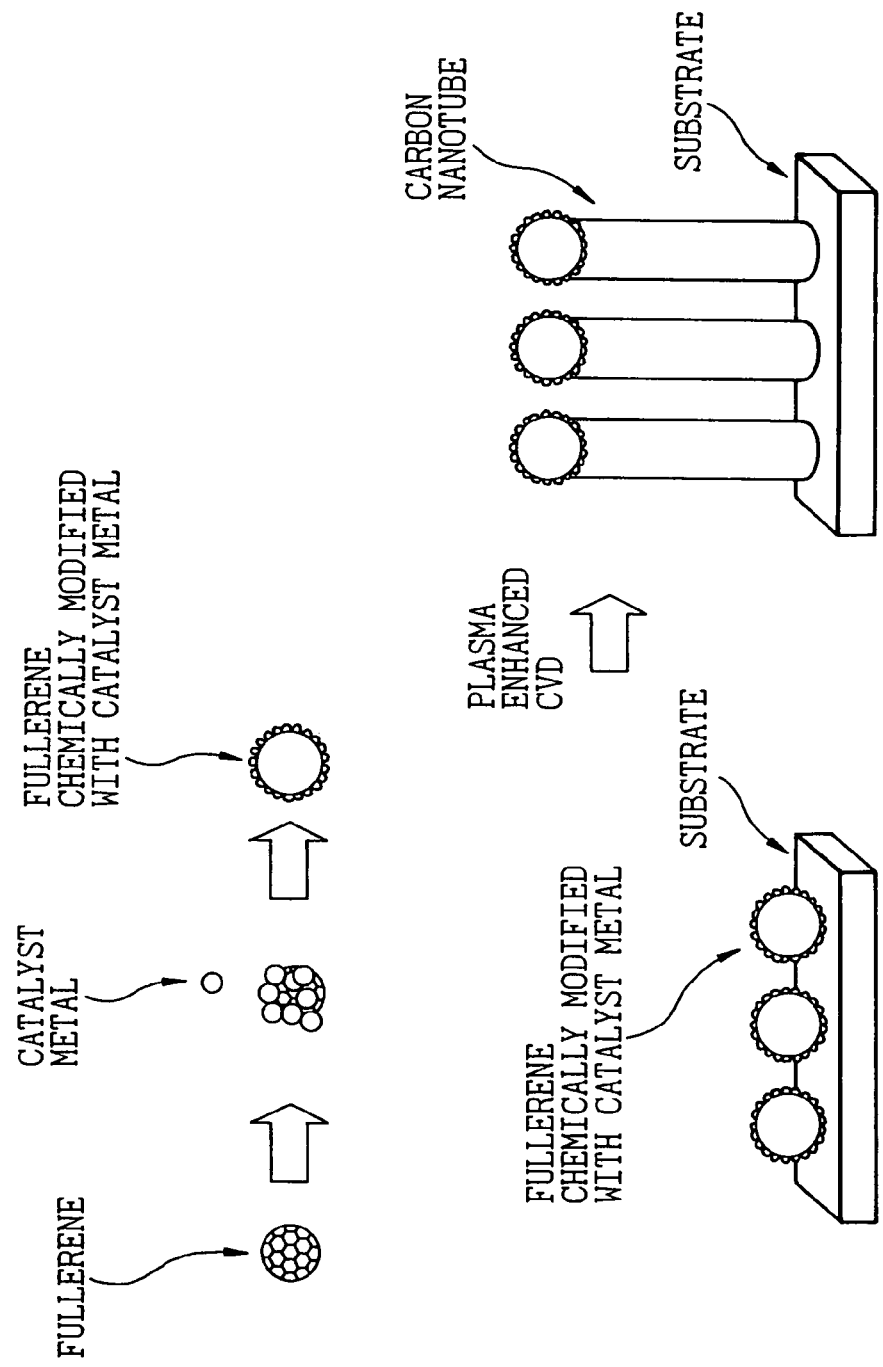

METHOD OF MANUFACTURING CARBON CYLINDRICAL STRUCTURES AND BIOPOLYMER DETECTION DEVICE

CROSS-REFERENCE TO RELATED APPLICATIONS

This application is a divisional of Ser. No. 10/303,083, filed Nov. 25, 2002 which is based upon and claims the benefit of priority from each of prior Japanese Patent Applications No. 2001-359661, filed on Nov. 26, 2001, No. 2001-387831, filed on Dec. 20, 2001, and No. 2002-077036, filed on Mar. 19, 2002, the entire contents thereof being incorporated herein by reference.

BACKGROUND OF THE INVENTION

1. Field of the Invention

The present invention relates to a method of manufacturing carbon cylindrical structures as represented by carbon nanotubes and, more particularly, to a method of manufacturing carbon cylindrical structures using a clean technology that is applicable to semiconductor electronics.

The present invention also relates to a method of efficiently manufacturing carbon nanotubes with controlled diameter and/or number of walls, and to single wall or multi-wall carbon nanotubes which are obtained by such a manufacturing method and which have uniform diameter and/or number of walls and thereby have uniform electrical properties.

The present invention further relates to a biopolymer detection device, and a biopolymer detection method, carbon nanotube structures used for same, and a disease diagnostic apparatus, which is capable of easily and reliably detecting a target biopolymer contained in a sample and which thereby permits diagnosis of a disease to be carried out efficiently.

2. Description of the Related Art

As a new carbon material, carbon nanotubes have attracted wide attention because of their unique physical properties. A carbon nanotube has a cylindrical structure of rolled-up graphite sheet in which hexagonal-shaped (six-membered ring) units of carbon atoms are bound to each other by $sp2^+$ bond, very strong bond between carbon atoms. Carbon nanotubes are nano-structures formed by carbon atoms in a self-organizing fashion, with the minimum diameter of 0.4 nm, and the length ranging as long as several hundreds μm, and are characterized by extremely small dimensional fluctuation. Electrical conductivity of a carbon nanotube varies widely from that of a semiconductor to that of a metal depending upon the chirality (the manner in which the graphite sheet is rolled up). In nanotubes exhibiting electrical conductivity of a metal, conduction by non-scattered charge carriers (ballistic conduction) is seen. In this case, the resistance value becomes independent of length, and the so-called quantum resistance (6.5 kΩ) is observed.

Possible application to various fields is envisaged for carbon nanotubes having such numerous characteristics. As an example, application to semiconductor electronics are being considered.

Several methods for manufacturing carbon nanotubes are known such as, for example, an arc discharge method, a laser ablation method, a thermal CVD method, a plasma enhanced CVD method, etc. In above-mentioned arc discharge method and laser ablation method, obtained carbon nanotubes include single wall carbon nanotubes (SWNT: Single Wall Nano Tube) that consists of a single graphite sheet, and multi-wall carbon nanotubes (MWNT: Multi Wall Nano Tube) that consists of a plurality of graphite sheets.

In thermal CVD methods and plasma enhanced CVD methods, MWNTs are produced predominantly. The above-mentioned SWNT has the structure in which a single graphen sheet of hexagonally linked carbon atoms bound via a strong bond called $sp2^+$ bond between carbon atoms is rolled up in the form of a tube. The carbon nanotube thus formed may have a diameter of 0.4 nm and length as long as several hundreds μm.

Regardless of the methods employed for manufacturing carbon nanotubes, control of chirality, control of diameter and control of length of the carbon nanotubes are problems remaining to be solved. Especially if these materials are to be applied to the field of semiconductor electronics, these problems have to be solved by using a clean technology.

Methods using arc discharge or laser ablation are not suited to mass production or to the manufacture of integrated circuits. In contrast, it can be said that methods using CVD for manufacturing carbon nanotubes may be applicable to semiconductor electronic device such as integrated circuits.

In CVD methods, a catalyst metal is considered to be necessary for growing carbon nanotubes. It has been reported that the diameter of the grown carbon nanotubes may be controlled by using the catalyst metal in the form of micro-particles and varying the size of the micro-particles. However, it has been found very difficult to fabricate the micro-particles of a catalyst metal with diameter controlled in the range of nanometers in accordance with the diameter of the carbon nanotubes. Thus, an alternative method is currently employed in which a catalyst metal film is formed on the growth substrate by sputtering or the like, and the surface of the metal film is bombarded with a high speed ion beam to produce a rugged structure of nanometer size on the surface, and the produced rugged structure is used in place of micro-particles of the catalyst metal. It can be easily surmised that it is difficult to form the rugged structure uniformly on the surface of the metal film so as to replace the micro-particles of the catalyst metal, especially when the diameter is small.

Another method is also attempted in which micro-particles are directly deposited on the surface of the substrate. In this method, coalescence of micro-particles takes place by collision of micro-particles with each other before they reach the substrate surface, or by diffusion of micro-particles on the substrate surface, and tends to produce secondary particles with larger diameters, so that it is difficult to produce smaller micro-particles.

In CVD methods, on the other hand, growth temperature of about 600 to 700° C. is usually employed. If a substrate having micro-particles of catalyst metal deposited thereon is heated to such a high temperature, the micro-particles may move, by rotation or the like, while the carbon nanotubes are growing so that it may twist the growing nanotubes or otherwise affect the chirality. Therefore, it is highly probable that the nanotubes having desired characteristics are extremely difficult to obtain.

On the other hand, the above-mentioned carbon nanotubes are nano-structures in which carbon atoms grow in self-organizing fashion, and as such, are characterized by extremely small dimensional fluctuation. It is also known that the electrical conductivity of the carbon nanotubes varies widely depending upon the difference of the manner of rolling-up of the tube (chirality) from that of a semiconductor to that of a metal. It is also known that, in the case of carbon nanotubes having the electrical conductivity of a metal, if there is no lattice defect, conduction of non-scattered charge carriers (ballistic conduction) is seen, and resistance value is the quantum resistance (6.5 kΩ) that is independent of length.

However, SWNTs grown in arc discharge method or laser ablation method are in the form of soot and contain a large amount of impurities so that refining to high purity is difficult and selective growth on a patterned substrate is impossible. On the other hand, selective growth on a patterned substrate is possible in a thermal CVD method or a plasma enhanced CVD method, and transition metals (for example, Ni, Co, Fe, etc.) are used in the form of a vapor deposition film, a sputtered film or ultra-fine particles as catalyst metals for carbon nanotubes.

When carbon nanotubes are grown on such a catalyst metal by a thermal CVD method or a plasma enhanced CVD method, the diameter of the grown nanotube is influenced by the grain boundaries, film thickness, or the like, of the thin film of the catalyst metal. Therefore, the diameter of the carbon nanotubes has been controlled by annealing of the catalyst metal to obtain finer particles. However, this method for obtaining finer particles of a catalyst metal has a drawback that the diameter of the catalyst metal cannot be made smaller than about several nm.

The Human Genome Project is a world-wide project in which various countries in the world have participated to analyze and determine the sequence of human genome (human DNA). It was started in 1990s, and in summer in the year 2000, a draft version was published containing complete sequencing information of human genome (DNA). If any part of this human genome (DNA) is correlated with some biological function of human body, it would bring about a new development in technology related to life science including disease diagnostics, disease therapy, etc.

For example, in conventional diagnosis of diabetes, only a broad classification into type I and type II diabetes has been done based on the insulin production capability of the patient's body. In the case of above-mentioned diabetes, the disease occurs as a result of inadequate regulation of blood sugar due to an imbalance of the function and amount of a plurality of proteins interacting with each other in complicated way, such as receptors of blood sugar and enzymes that synthesize or decompose insulin in accordance with the value of blood sugar. In conventional diagnosis of diabetes, however, there is a problem that the direct cause of the diabetes cannot be known. But, the sequencing information of human genome (DNA) obtained by the Human Genome Project offers us the complete information about the genes (DNA) encoding amino acid sequence of various proteins such as the receptors and enzymes involved in the regulation of the blood sugar value. Thus, by analyzing the gene (DNA) information, we can know the protein directly responsible to the anomalous regulation of the blood sugar value, so that, instead of the broad classification of the diabetes into diabetes of type I and type II, diabetes can be classified more specifically into subtypes, and more suitable diagnosis and therapy of the diabetes would become thereby possible. It is expected that, in the near future, diagnosis and therapy of a disease can be carried out in more suitable manner by analyzing the function and amount of a plurality of proteins in close functional relation with each other.

At present, no established method capable of quickly determining the amount of a plurality of proteins in close functional relation with each other, as described above, is known except for the method that combines two dimensional electrophoresis with mass spectroscopy. However, even with this method, there are problems that effective information for diagnosis and therapy of a disease cannot be obtained sufficiently and measurement cannot be carried out quickly.

On the other hand, as regards DNA, a DNA chip has been provided that is capable of quickly quantifying the amount of DNA in a sample. This is done by introducing in advance a fluorescent labeling dye during the amplification (increase of amount) by PCR (polymerase chain reaction) of the DNA to be measured, and by measuring the fluorescent light intensity based on the DNA in the sample bound to the complementary DNA arranged in an array. However, as for proteins, there is no amplification method for proteins corresponding to the PCR method for DNA, and in addition, reactivity with a fluorescent labeling dye is different for different proteins so that it is difficult to introduce a fluorescent labeling dye uniformly to various proteins. For these reasons, a chip capable of quantifying the amount of proteins in a sample has not been provided until now. Therefore, it is desired to develop an array chip and associated technology capable of quickly quantifying the amount of a specific protein without using a fluorescent labeling dye.

SUMMARY OF THE INVENTION

It is an object of the present invention to provide a method of manufacturing carbon cylindrical structures as represented by carbon nanotubes using a substrate having deposited thereon micro-particles of a catalyst metal for CVD growth of carbon cylindrical structures without forming secondary particles of larger diameter, and using a clean dust-free technology that is capable of being applied to a semiconductor electronic device.

It is another object of the present invention to provide a method of manufacturing carbon nanotubes, which permits carbon nanotubes with controlled diameter and/or controlled number of walls to be manufactured efficiently, and to provide single wall or multi-wall carbon nanotubes obtained by the above-mentioned manufacturing method, and having a uniform diameter and/or a uniform number of walls.

It is a further object of the present invention to provide a biopolymer detection device and a biopolymer detection method which is capable of easily, reliably and quickly detecting the amount of a plurality of target biopolymers present in a sample in close functional relation with each other and which is capable of being applied to an array chip technology, and to provide carbon nanotube structures used for same, and a disease diagnosis apparatus using same.

In accordance with a first aspect of the present invention, there is provided a method of manufacturing carbon cylindrical structures using chemical vapor deposition (CVD) process to grow and manufacture the carbon cylindrical structures on a substrate, characterized in that metal ions are implanted to the substrate and then the carbon cylindrical structures are caused to grow using the metal ions as a catalyst.

In accordance with a second aspect of the present invention, there is provided a method of manufacturing carbon nanotubes as described below.

(1) A method of manufacturing carbon nanotubes, characterized in that nano-carbon material is used as the seed material for growing carbon nanotubes. In the method of manufacturing carbon nanotubes as described in (1), nano-carbon material with uniform diameter is used as seed material. It is possible to efficiently manufacture carbon nanotubes having uniform diameter and/or uniform number of walls by growing carbon nanotubes from this seed material. The carbon nanotubes with uniform diameter and/or uniform number of walls have uniform electrical characteristics so that they can be used in various fields, for example, in electronics material such as a field emission type display, fluorescent display lamp, etc., in energy material such as a fuel cell, a lithium ion battery, etc., in composite material such as reinforced plastic, anti-static agent, reinforced plastic, etc., in nano-technology material such as a nano-device, a probe in a scanning probe microscope, a DNA chip, etc.

(2) A method of manufacturing carbon nanotubes according to the method (1), wherein nano-carbon material is disposed on the substrate and the carbon nanotubes are selectively grown in a direction generally perpendicular to the substrate. According to the method of manufacturing carbon nanotubes as described in (2), carbon nanotubes with uniform diameter and/or uniform number of walls can be directly formed on the substrate, and need for operations such as refining can be eliminated. The carbon nanotubes can be formed on the substrate as aligned in a direction perpendicular to the substrate. Further, the carbon nanotubes can be formed in high density and in high precision selectively at an optional position on the substrate.

(3) A method of manufacturing carbon nanotubes according to the method (1) or (2), wherein selective growth is carried out by a CVD method. In the method of manufacturing carbon nanotubes as described in (3), the carbon nanotubes can be selectively grown at an arbitrary position on the substrate in a direction perpendicular to the substrate.

(4) A method of manufacturing carbon nanotubes according to any one of the methods (1) to (3), wherein the nano-carbon material consists of a coating with a catalyst metal. In the method of manufacturing carbon nanotubes as described in (4), the nano-carbon material as seed material is chemically modified or coated with a metal so that growth of the carbon nanotubes may be carried out efficiently by catalytic action of the metal.

(5) A method of manufacturing carbon nanotubes according to the method (4), wherein the catalyst metal is at least one of a transition metal and a transition metal compound. In the method of manufacturing carbon nanotubes as described in (5), when the metal of the nano-carbon material that is chemically modified or coated with a catalyst metal is a transition metal or transition metal compound, growth of the carbon nanotubes may be carried out efficiently by catalytic action of the metal using the nano-carbon material containing the metal as seed material.

(6) A method of manufacturing carbon nanotubes according to any one of the methods (1) to (5), wherein diameter of the carbon nanotube is controlled by controlling the diameter of the nano-carbon material. In the method of manufacturing carbon nanotubes as described in (6), by controlling diameter of the nano-carbon material as seed material, the diameter and/or number of walls of the carbon nanotubes grown from the seed material can be controlled.

(7) A method of manufacturing carbon nanotubes according to any one of the methods (1) to (6), wherein the number of walls of the multi-wall carbon nanotubes is controlled by controlling the thickness of the catalyst metal layer of the nano-carbon material coated with the catalyst metal. In the method of manufacturing carbon nanotubes as described in (7), the nano-carbon material as seed material is arranged periodically on the substrate and the carbon nanotubes are grown from the periodically arranged seed material so that the carbon nanotubes having uniform diameter and/or uniform number of walls and arranged periodically in high precision can be obtained.

(8) A method of manufacturing carbon nanotubes according to any one of the methods (1) to (7), wherein the nano-carbon material is fullerene. In the method of manufacturing carbon nanotubes as described in (8), fullerene is used as the nano-carbon material. As fullerene is higher in purity and smaller in diameter among various nano-carbon materials, it is suited to the manufacture of carbon nanotubes of uniform diameter and/or uniform number of walls.

(9) Carbon nanotubes obtained by any one of the manufacturing methods (1) to (8), characterized in that the carbon nanotubes have single wall structure. The single wall carbon nanotubes, as described in (9), are uniform in diameter, and hence uniform in electrical characteristics.

(10) Carbon nanotubes obtained by any one of the manufacturing methods (1) to (8), characterized in that the carbon nanotubes have multi-wall structure. The multi-wall carbon nanotubes as described in (10), are uniform in diameter and/or number of walls, and hence uniform in electrical characteristics.

On the other hand, a biopolymer detection device according to the present invention is as described below.

(a) A biopolymer detection device comprising vibration inducing means for inducing vibration, binding means capable of resonating with the vibration induced by the vibration inducing means and capable of binding or interacting with target biopolymers, and detection means for detecting whether or not the binding means binds or interact with the target biopolymers.

In the biopolymer detection device as described in (a), the vibration inducing means induce vibration. The binding means resonate with the vibration induced by the vibration inducing means. The binding means are capable of binding or interacting with a target biopolymer, so that, if the target biopolymer is contained in a sample, the binding means bind or interact with the target biopolymer. Content of the target biopolymer can be quickly quantified by the detection means that detect whether or not the binding means bind or interact with the target biopolymer.

(b) A biopolymer detection device according to (a), wherein the vibration inducing means comprise a base electrode provided at one end of the binding means, a vibration inducing electrode disposed near the binding means, and an alternating current (AC) power source connected conductively to the base electrode and the vibration inducing electrode and capable of applying an AC voltage.

In the biopolymer detection device as described in (b), the base electrode is provided at one end of the binding means and the vibration inducing electrode is disposed near the binding means with the two electrodes not connected in complete electrical conduction with each other, so that, when the AC power source applies an AC voltage, an AC electric field is produced between the binding means and the vibration inducing electrode and the binding means thereby vibrate due to its electrical conduction in accordance with the frequency of applied AC voltage.

(c) A biopolymer detection device according to (a) or (b), wherein a piezoelectric element is used as the vibration inducing means. In the biopolymer detection device according to (c), when the piezoelectric element is driven, the binding means resonate with the vibration induced by the piezoelectric element.

(d) A biopolymer detection device according to any one of (a) to (c), wherein the binding means comprise a responding part capable of resonating with the vibration applied by the vibration inducing means, and a binding part capable of binding and/or interacting with the target biopolymer. In the biopolymer detection device according to (d), the responding part resonates with the vibration induced by the vibration inducing means. When the target biopolymer is contained in the sample, the binding part binds or interacts with the target biopolymer.

(e) A biopolymer detection device according to (d) above, wherein the responding part is a carbon nanotube. In the biopolymer detection device according to (e), the carbon nanotube resonates with the vibration induced by the vibration inducing means.

(f) A biopolymer detection device according to any one of (c) to (e), wherein the binding means comprise a binding part bound to the tip of the carbon nanotube manufactured by reacting and binding the material which forms binding part with dangling bond at the tip of the carbon nanotube produced by processing the carbon nanotube. In the biopolymer detection device according to (f), the carbon nanotube resonates with the vibration induced by the vibration inducing means. The binding part that is bound to the tip of the carbon nanotube by reacting the material which forms the binding part with the dangling bond produced by processing under oxygen plasma atmosphere, binds or interacts with the target biopolymer when the target biopolymer is contained in the sample.

(g) A biopolymer detection device according to any one of (d) to (f), wherein the binding part is selected as at least one of substances, antibodies and fragments of antibodies capable of binding or interacting with the target biopolymer under physiological conditions. In the biopolymer detection device according to (g), the binding part is capable of specifically binding or interacting with a target biopolymer so that a specific target biopolymer can be quickly quantified.

A biopolymer detection method according to the present invention is a biopolymer detection method comprising the steps of a vibration inducing step of inducing vibration in binding means capable of binding or interacting with a target biopolymer, and a detection step of detecting the change of vibration in the binding means when the binding means are bound with the target biopolymer.

In this biopolymer detection method, vibration is induced in the binding means in the vibration inducing step. The binding means are capable of binding or interacting with a target biopolymer so that, when the target biopolymer is contained in the sample, the binding means bind or interact with the target biopolymer. In the detection step, it is detected whether or not the binding means bind or interact with the target polymer. As a result, the amount of the target biopolymer is quickly quantified.

A carbon nanotube structure according to the present invention is a carbon nanotube structure comprising a binding part capable of binding or interacting with a target biopolymer at the tip of the carbon nanotube, and manufactured by reacting and binding the material which forms the binding part with dangling bond at the tip of the carbon nanotube produced by processing the carbon nanotube. This carbon nanotube can be advantageously used for above-mentioned biopolymer detection device, in above-mentioned biopolymer detection method, etc.

A disease diagnosis apparatus according to the present invention is a disease diagnosis apparatus comprising the biopolymer detection device according to any one of (1) to (7) above. Since this disease diagnosis apparatus comprises the above-mentioned biopolymer detection device, the content of a protein responsible for a disease in a sample as the above-mentioned target biopolymer can be quantified in a short time and the disease can be thereby diagnosed easily and specifically.

BRIEF DESCRIPTION OF THE DRAWINGS

FIG. 3 is a schematic explanatory view showing an example of the method of manufacturing carbon nanotubes step by step according to example 3;

DETAILED DESCRIPTION OF THE INVENTION

In accordance with the first aspect of the present invention, there is provided a method of manufacturing carbon cylindrical structures by using a CVD method to grow carbon cylindrical structures on a substrate. A carbon cylindrical structure, as used herein, refers to a structure as represented by a structure called carbon nanotube in which a graphite sheet composed of six-membered units of carbon atoms bound with each other via sp2 bond, is rolled-up in the form of a tube. Hereinafter, these structures are referred to as carbon nanotubes.

In the manufacture of carbon nanotubes by a CVD method, a catalyst, usually a transition metal catalyst such as iron, nickel, cobalt, etc., is required. In the present invention, such a catalyst metal is introduced to the growth substrate by ion implantation method. Ion implantation method is used in the manufacture of semiconductor electronic devices as a method for doping impurities into a semiconductor, and as such, is a clean dust-free technology. In ion implantation method, a catalyst metal atom reaches the substrate in the form of an ionized atom, and penetrates into the substrate to be scattered by substrate atoms and thereby loses its energy to settle into the final position. Therefore, the implanted metal ions do not form a secondary particle, and can be each fixed and held in the substrate as an independent atom at the smallest form. Further, the density can be controlled by the dose of the ion implantation. In addition, if necessary, heating may be performed after implantation of ions to promote diffusion of ions and to form clusters as secondary particles. When clusters are formed, the diameter of the cluster has to be controlled in accordance with the diameter of the nanotubes to be grown, and is, in general, preferably not greater than 20 nm.

The first and the basic aspect of the present invention will now be described with reference to FIGS. 1A to 1D.

Figure 1A:
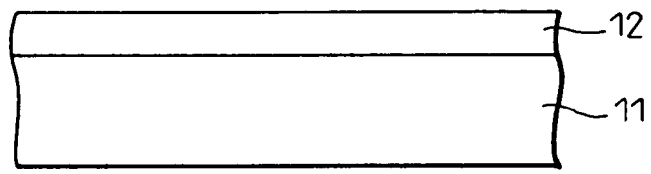
FIGS. 1A to 1D are views useful for explaining a method of manufacturing carbon cylindrical structures according to a first aspect of the present invention.

First, as shown in FIG. 1A, a film 12 called a mask is formed on the substrate 11.

A semiconductor such as silicon, or a metal, may be used as the substrate 11. In either case, the substrate 11 may be formed on different material, for example, a metal film formed on silicon or a silicon film formed on a metal may be used as the substrate. When a metal is used as the substrate 11, it is advantageous in that the contact resistance between the substrate 11 and the nanotube grown on the substrate is reduced.

The mask film 12 serves to bring the peak of the distribution of implanted ions in the depth direction to the interface between the substrate 11 and the mask film 12. The mask film 12 may be formed from arbitrary material that can effectively decelerate the implanted ions. Useful material for the film 12 includes not only those materials typically used in the manufacturing process of semiconductor devices such as a resist, silicon oxide film, silicon nitride film, silicon oxide nitride film, etc., but also ceramic materials such as alumina, and metallic materials provided that they do not serve as catalyst during the subsequent process of the carbon nanotube growth.

The peak of the distribution of implanted ions in the depth direction can be calculated using LSS theory from the material and thickness of the mask film 12 and the implanted ion species and the energy of implantation, etc. Therefore, the peak can be easily brought to the interface between the substrate 11 and the mask film 12. Thus, the position of the peak can be easily controlled by controlling, for example, the accelerating energy of implantation and the thickness of the mask film.

Figure 1B:
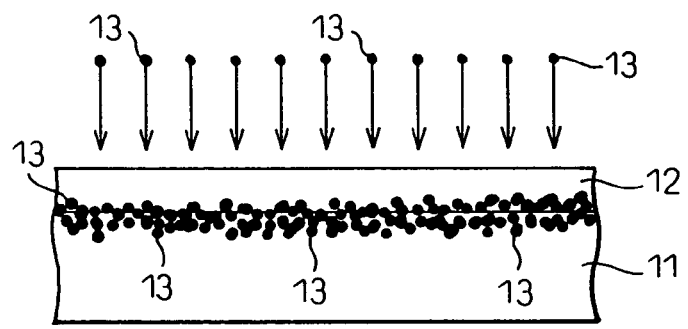

Next, as shown in FIG. 1B, the catalyst metal ions 13 are implanted at a predetermined energy. The implanted ions 13 are thereby finally arranged and predominantly concentrated at the interface between the substrate 11 and the film 12. The density of implanted ions can be controlled by the dose (duration of implantation) of the ion implantation. If necessary, heating may be performed after implantation to promote the diffusion of ions so that clusters can be formed and secondary particles of a predetermined diameter can be obtained.

Figure 1C:
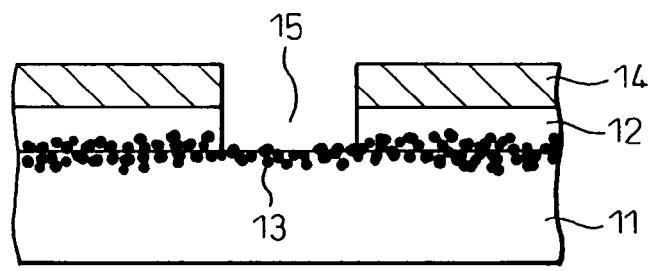
Figure 1D:
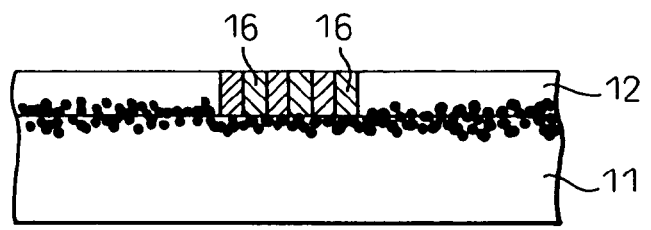

Then, as shown in FIG. 1C, a resist film 14 formed with a predetermined opening pattern is patterned onto the mask film 12, and an opening 15 is formed in the film 12 and the substrate 11 is exposed at the bottom thereof. The portion of implanted ions contained in the film 12 is removed together with the portion of the film 12 removed by the patterning, leaving implanted ions 13 at the surface (and the underlying portion) of the exposed portion of the substrate 11.

After removing the resist film 14, carbon nanotubes 16 are grown by a CVD method using the implanted ions 13 as a catalyst.

Carbon nanotubes can be grown either by a plasma enhanced CVD method or by a thermal CVD method. In the present invention, either method may be used. These CVD methods are well known, and need not be explained specifically. Only as an example, a plasma enhanced CVD method may be carried out by causing methane ($CH_4$) gas and hydrogen ($H_2$) gas to flow at about 650° C. under reduced pressure. A thermal CVD method may be also carried out by causing acetylene ($C_2H_2$) gas and hydrogen gas to flow at about 650° C. under reduced pressure. It is known that, in the growth of carbon nanotubes by a CVD method, presence of an electric field in the same direction as the growing direction is effective for the control of the growth direction of the carbon nanotubes. Therefore, irrespective of whether a plasma enhanced CVD or a thermal CVD method is adopted, an electric field is preferably applied in the direction of the growing direction of the tube, that is, in a direction perpendicular to the surface of the substrate. In either case, a transition metal such as iron, nickel, cobalt, etc., may be used as a catalyst metal for the growth. Here, the catalyst can be formed in the size ranging from the size of a single atom to about 20 nm, so that carbon nanotubes which grow with desired diameter can be obtained accordingly.

Thus, in the method of the present invention, before growing carbon nanotubes, a portion of mask film is removed to expose surface of the substrate that contains the implanted catalyst metal ions, and carbon nanotubes are grown using the catalyst metal as nuclei. Removal of the mask film is selectively accomplished as necessary by forming a patterned resist film and by etching using same so that the growth position of the nanotubes can be controlled. When, for example, a silicon oxide film is used as a mask film, etching technique using a fluorine etchant can be applied.

Simulation of the density distribution of the implanted ions in the depth direction was performed for the case of silicon oxide used as a mask film, and Ni, Fe, or Co used as a catalyst metal with accelerating energy of 65 to 85 keV. As a result of the simulation, it was found that, when a silicon oxide film of 50 nm in thickness was used as a mask film, the peak of the density distribution was brought approximately into the vicinity of the interface between the substrate and the mask. Here, the substrate was assumed to be silicon. When the dose of the implanted ions was $1\times10^{16}/cm^2$, the ion density at the peak depth amounted to about $10^{21}/cm^3$. This density can be controlled by varying the dose, and amounts to about $10^{20}/cm^3$ when the dose is $1\times10^{15}/cm^2$. Thus, the density of nanotubes can be increased by increasing the dose further.

Next, the second aspect of the present invention will be described with reference to FIGS. 2A to 2D. In the first aspect of the present invention as described above with reference to FIGS. 1A to 1D, the implanted metal ions are left in the region where carbon nanotubes need not be grown. In contrast, in the second aspect of the invention to be described below, the carbon nanotubes can be grown only in the desired region without leaving the implanted ions in an unnecessary region.

Figure 2A:
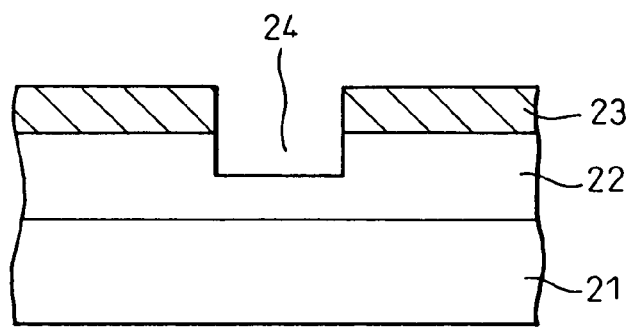
FIGS. 2A to 2D are views useful for explaining a method of manufacturing carbon cylindrical structures according to a second aspect of the present invention.

First, as shown in FIG. 2A, a film 22 is formed on the substrate 21 as a mask for ion implantation, and, using a resist pattern 23 provided thereon as a mask, the film 22 exposed in the resist pattern opening is etched to the midway in the thickness direction so that the thickness of the film 22 in the region where carbon nanotubes are to be grown later is adapted to concentrate the implanted metal ions to the interface between the film 22 and the substrate 21. Thus, after etching, the film 22 has recess 24 corresponding to the carbon nanotube growth region.

Figure 2B:
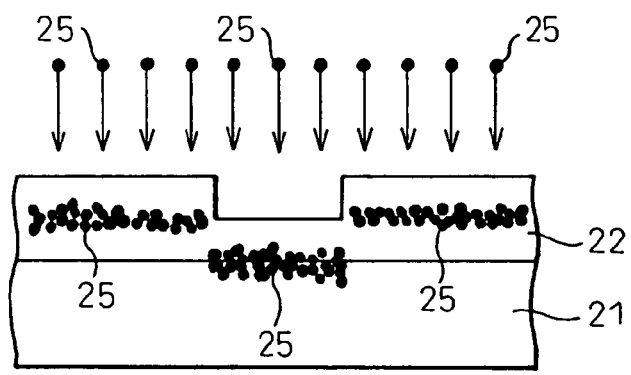

Next, as shown in FIG. 2B, a catalyst metal ions 25 are implanted at a predetermined energy through the film 22. As the thickness of the film 22 is different depending upon the location, ions implanted in the recess 24 of the film 22 are concentrated at the vicinity of the interface between the substrate 21 and the film 22 while ions implanted in other region are stopped in the midway in the film 22 and do not reach the interface. The resist pattern 23 (FIG. 2A) may be removed before or after the ion implantation.

Figure 2C:
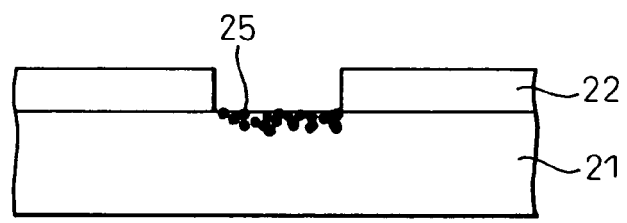
Figure 2D:
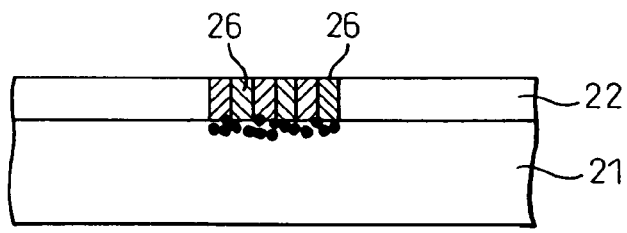

Then, etching of the film 22 is performed, as shown in FIG. 2C, until the surface of the substrate 21 containing the implanted ions 25 is exposed in the recess 24 (FIG. 2B) corresponding to the carbon nanotube growth region. As the depth of the recess 24 has been controlled when forming the recess 24 in the film 22 as explained in FIG. 2A, the ions implanted in region other than the recess 24 and stopped in the midway in the film 22 can be removed advantageously in this etching of the film 22 together with the film material.

Then, a CVD method can be used to grow carbon nanotubes 26 on the substrate 21 using the metal ions on the exposed surface of the substrate 21 as a catalyst. This growth process may be performed as has been described with reference to FIG. 1D.

Implantation of metal ions may be performed by any ion implantation method. In the method as described above, ions are implanted to the entire surface of the mask film on the substrate. But, by using an implantation method such as, for example, focused ion beam method, ions can be implanted only to a specific area, and the process of removing metal ions remaining in the mask film other than the carbon nanotube growth region.

Thus, in accordance with the method of the present invention, by combining a dust-free and clean technology which has been widely utilized in the manufacture of semiconductor devices, etc., that is, lithography and ion implantation, with a CVD technology which has also been used conventionally, carbon nanotubes can be manufactured on a substrate, and therefore, the process modification can be easily made using existing equipments.

The surface of the substrate immediately after the ion implantation is in amorphous state due to damage caused by the ion accelerating energy. However, the implanted metal ions which are to serve as catalyst for carbon nanotube growth by CVD method, are partially embedded in the substrate, and are not so unstable as the conventional metal particles that have been simply deposited and rest on the substrate surface, but are fixed in position and remain stable during the growth of carbon nanotubes at high temperature. This is considered to be effective in suppressing the possible change of chirality or twisting of nanotubes caused by the positional instability of the catalyst metal during the growth of the nanotubes.

In the method of manufacturing carbon nanotubes in accordance with the second aspect of the present invention, nano-carbon material is used as the seed material for growing carbon nanotubes. Thus, in the method of manufacturing carbon nanotubes according to the present invention, nano-carbon material is disposed on a substrate, and using the nano-carbon material as seed material, carbon nanotubes are selectively grown in a direction perpendicular to the substrate.

The nano-carbon material is not particularly restricted as long as it can be used as seed material for growing carbon nanotubes, and may be suitably selected depending upon the intended application from any of the known carbon material, for example, fullerene, carbon black, acetylene black, ketjen black, natural graphite (flake graphite, earthy graphite), synthetic graphite. Among these, fullerene and carbon black may be preferably used. Average particle diameter of the nano-carbon material is not particularly restricted, and is preferably in the range of 0.4 to 100 nm.

The fullerene may be, for example, $C_{36}$, $C_{60}$, $C_{70}$, $C_{76}$, $C_{78}$, $C_{80}$, $C_{82}$, $C_{84}$, and is preferably $C_{60}$ in view of high purity, uniform diameter, ease of handling, and the like. The fullerene can be mass-synthesized by known arc discharge method using carbon electrodes.

The nano-carbon material is preferably used after chemical modification with a compound containing a catalyst metal, or after coating from outside with a catalyst metal in order to exhibit the catalytic activity of the catalyst metal in the growth of carbon nanotubes.

The method of chemical modification with a catalyst metal is not particularly restricted, and may be suitably selected depending upon the intended application from any methods. For example, the nano-carbon material can be contacted with a solution containing metal ions, surface active agents, etc., so that the metal ions may be adsorbed and supported on the surface of the nano-carbon material. The solvent is not particularly restricted, and toluene, benzene, carbon disulfide, or water, for example, can be advantageously used.

The surface active agent may be, for example, cyclodextrin, lecithin, polyvinyl pyrrolidone, etc.

Method for coating the nano-carbon material from outside with a catalyst metal is not particularly restricted as long as it can control the thickness of the coating, and may be suitably selected depending upon the intended application from any methods, such as vapor deposition method, sputtering method, etc.

In this case, by controlling the thickness of the catalyst metal layer coated on the nano-carbon material, that is, by controlling the diameter of the nano-carbon material including the catalyst metal layer, the diameter and/or number of walls of the carbon nanotubes can be controlled.

The thickness of the catalyst metal (amount of the catalyst metal) is not particularly restricted, and may be selected suitably depending upon the intended application, and is preferably, for example, in the range of 1 nm to 100 nm.

The number of walls of the carbon nanotubes can also be controlled by controlling the thickness of the catalyst metal layer coated on the nano-carbon material (that is, the overall diameter of the nano-carbon material including the thickness of the catalyst metal layer).

For example, if the thickness of the catalyst metal layer is 3 nm or less, single wall carbon nanotubes can be manufactured. If the thickness of the catalyst metal layer is greater than 10 nm, multi-wall carbon nanotubes with two or more walls can be manufactured.

The catalyst metal is not particularly restricted as long as the metal has catalytic activity, and may be suitably selected depending upon the intended application. A transition metal or transition metal compound is preferably used.

The transition metal may be, for example, Al, Ti, V, Cr, Mn, Fe, Ni, Co, Cu, Zn, Zr, Mo, Ru, Rh, Pd, Ag, Cd, In, Sn, Sb, W, Re, Os, Ir, Pt, or alloys containing these metal elements, and among them, Fe, Co, Ni are preferable in view of high catalytic activity.

The transition metal compound may be oxides, halides, hydroxides, sulfates, nitrates of the transition metal.

Average diameter of the catalyst metal is not particularly restricted, and may be selected suitably depending upon the intended application, and is typically in the range of about 1 to 100 nm.

The substrate is not particularly restricted, and any commonly used substrate, for example, a Si substrate, a glass substrate, a quartz substrate, an alumina substrate, a porous silica substrate, an alumina plate processed in anodic oxidation, can be used.

In the manufacture of carbon nanotubes, the surface of the substrate is preferably cleaned thoroughly. As the cleaning method, in addition to washing by solvent, a discharge processing such as corona processing, plasma processing and plasma ashing etc., is advantageously used. A combination of several cleaning methods can be used to achieve an improved cleaning effect.

Method of disposing the nano-carbon material as seed material on the substrate is not particularly restricted, and may be selected suitably depending upon the intended application. For example, a coating solution containing the seed material may be coated on the substrate, and patterned by means of a lithography method to dispose the seed material at an optional position on the substrate. The seed material may be arranged periodically on a substrate to obtain carbon nanotubes arranged at high density and with high precision.

In the method of manufacturing carbon nanotubes according to the present invention, the method of selectively growing carbon nanotubes from the seed material disposed on the substrate is not particularly restricted, and may be selected suitably depending upon the intended application. In particular, a CVD (chemical vapor deposition) method is preferable in that the carbon nanotubes can be grown selectively in a direction perpendicular to the substrate.

The CVD method (chemical vapor deposition method) includes, for example, a thermal CVD (also called simply as CVD), a hot filament CVD, plasma enhanced CVD (also called as plasma assisted CVD, or plasma CVD), a plasma enhanced hot filament CVD, a laser enhanced CVD (also called as laser CVD). Among them, a thermal CVD and a plasma enhanced CVD are preferable.

In the thermal CVD, the temperature of the filament is about 500 to 2000° C., and decomposition of the raw material gas is promoted by the heat from the filament.

In the plasma enhanced CVD, in general, a high frequency field (RF) is advantageously used to excite plasma, but a low frequency field, a microwave field (MW) or a direct current field (DC) may also be used.

In this method, decomposition of the raw material gas is enhanced by the plasma. Output power of the high frequency plasma is in the range of about 0.1 to 1000 W/cm$^3$.

The condition for the selective growth of carbon nanotubes in the CVD method is not particularly restricted, and similar condition used in the manufacture of carbon nanotubes in an ordinary CVD method may be suitably adopted.

In this case, the process is preferably controlled by mass flow rate of the raw material gas. As the raw material gas, a gas mixture of a carbon supply gas and an introducing gas is advantageously used.

The carbon supply gas may be, for example, methane, ethylene, acetylene, benzene, butane, isopropanol, $C_{10}H_{16}$, $CS_2$, $C_{60}$, etc.

The introducing gas may be hydrogen, $NH_3$, etc.

Here, blending ratio of the gas mixture is not particularly restricted, and may be selected suitably depending upon the intended application. For example, when methane gas is used as carbon supply gas and hydrogen gas is used as introducing gas, the mass flow ratio is preferably in the range of methane gas:hydrogen gas=1 to 5:9 to 5.

Pressure in the vacuum chamber is preferably in the range of 1 to 10 Torr.

In a specific example of the method of manufacturing carbon nanotubes according to the present invention as shown in FIG. 3, fullerene is dispersed in a solvent such as methanol, IPA, toluene, etc., and a compound containing a catalyst metal is mixed into the solution to chemically modify the fullerene with a catalyst metal such as Fe, Co, Ni to obtain the seed material. This seed material is disposed on a substrate such as silicon, and carbon nanotubes are selectively grown by a plasma enhanced CVD method.

As a consequence, in the plasma CVD method, the catalyst metal is left at the tip portion. By using fullerene chemically modified with the catalyst metal, carbon nanotubes having uniformly controlled diameter can be selectively grown.

Figure 7:
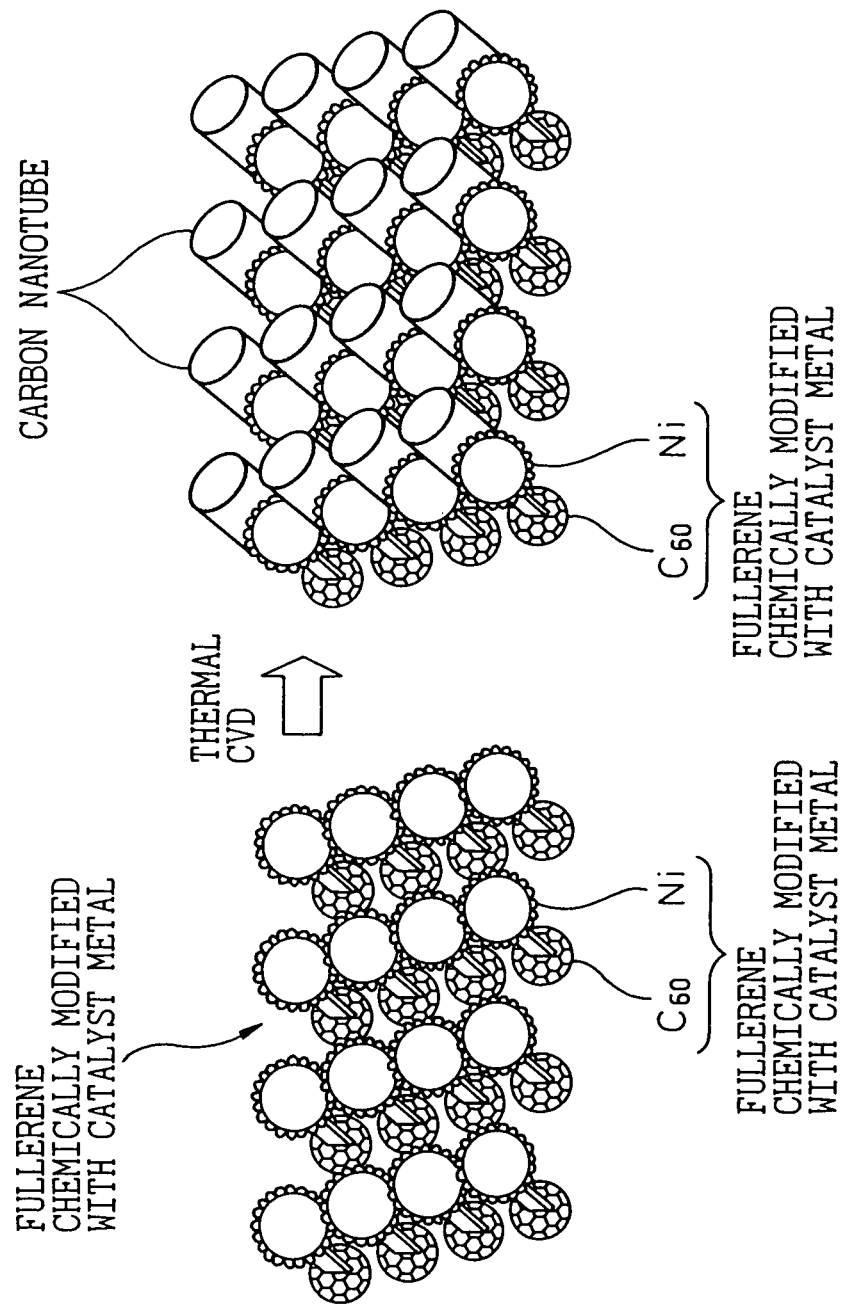
FIG. 7 is a schematic explanatory view showing a method of manufacturing carbon nanotubes according to example 5.

By using a substrate having the nano-carbon material as seed material arranged periodically, carbon nanotubes which are arranged periodically in high precision and in high density on the substrate can be obtained (see FIG. 7).

In the method of manufacturing carbon nanotubes according to the present invention, by controlling the thickness of the catalyst metal layer coated on fullerene, the diameter of carbon nanotubes and the number of walls of multi-wall carbon nanotubes can be controlled.

Figure 6A:
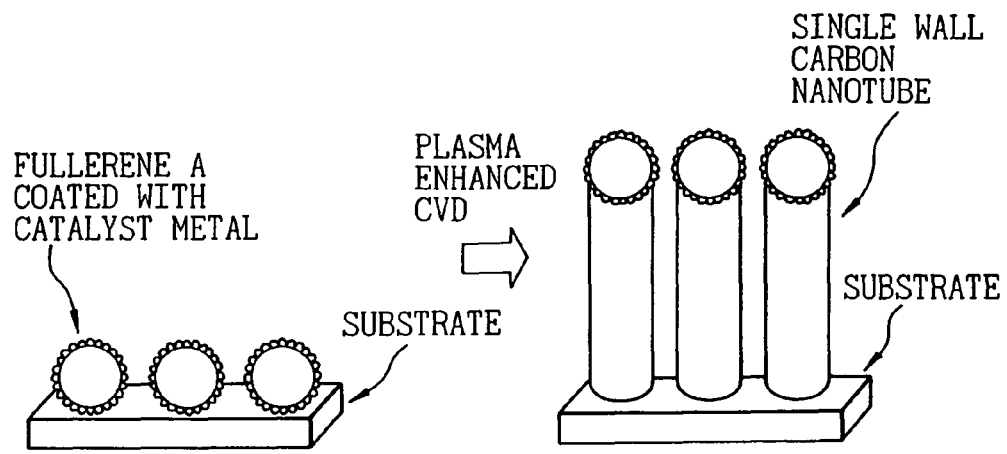
FIGS. 6A and 6B are a schematic explanatory view showing a method of manufacturing carbon nanotubes according to example 4.

For example, as shown in FIG. 6A, a catalyst metal is coated to fullerene by vapor deposition or sputtering. If fullerene A having the thickness of coated catalyst metal layer controlled to 3 nm or less (seed material) is disposed on a substrate and carbon nanotubes are grown by plasma enhanced CVD method, single wall carbon nanotubes are obtained.

Figure 6B:
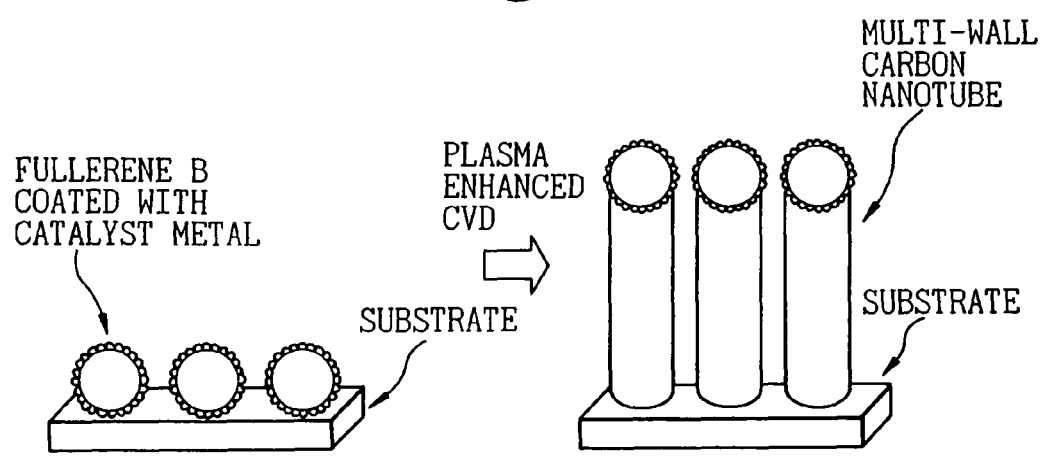

If, as shown in FIG. 6B, fullerene B having the thickness of coated catalyst metal layer controlled to 10 nm (seed material) is disposed on a substrate and carbon nanotubes are grown by plasma enhanced CVD method, multi-wall carbon nanotubes are obtained.

The single wall carbon nanotubes obtained by the method of manufacturing carbon nanotubes according to the present invention are uniform in diameter. The diameter is about 0.4 to 3 nm, and the length is about 10 nm to 10 μm.

The multi-wall carbon nanotubes obtained by the method of manufacturing carbon nanotubes according to the present invention are uniform in diameter and/or number of walls. The diameter is about 3 to 100 nm, the length is about 10 nm to 10 μm, and the number of walls is 2 to 100.

The carbon nanotubes obtained by the method of manufacturing carbon nanotubes according to the present invention are uniform in diameter and/or number of walls, and can be arranged periodically in high precision and in high density on the substrate. Therefore, they exhibit uniform electrical characteristics, and can be applied widely in various fields as electronic material for a field emission type display, a fluorescent indicator lamp, as energy material such as a fuel cell, lithium ion battery, as composite material such as reinforced plastic, anti-static agent, reinforced plastic, and as nano-technology material such as nano-device, a probe for a scanning type probe microscope, a DNA chip, etc.

A biopolymer detection device according to the present invention comprises vibration inducing means, binding means, and detection means, and further comprises suitably selected other means as required.

The vibration inducing means are not particularly restricted as long as they have the function of inducing vibration, and may be suitably selected from any known means depending upon the intended application. The vibration inducing means are preferably capable of inducing vibration by at least one of the means having frequencies selected from the group consisting of electric field, electric current, acoustic, magnetic, optical and mechanical stimulations.

The vibration inducing means capable of inducing vibration by electric current may be preferably an electric circuit, or a piezoelectric element, comprising, for example, a base electrode provided at one end of the binding means, a vibration inducing electrode disposed near the binding means, and an alternating current (AC) power source conductively connected to the base electrode and to the vibration inducing electrode and capable of applying an AC voltage. In the electric circuit, preferably the base electrode is fixed, the binding means are disposed in a standing position, and the vibration inducing electrode is disposed near the circumferential side of the binding means. In this case, when an AC voltage is applied to the base electrode and the vibration inducing electrode by the AC power source, the binding means can be vibrated in horizontal direction in accordance with the frequency of the AC voltage.

The vibration inducing means capable of inducing vibration by acoustic wave may be preferably, for example, an ultrasonic oscillator. In the case of an ultrasonic oscillator, the binding means can be vibrated in accordance with the frequency of the ultrasonic wave generated by the ultrasonic oscillator.

The vibration inducing means capable of inducing vibration by magnetic means may be preferably, for example, a rotatable permanent magnet, or an electromagnet, having both poles and disposed near the binding means to which magnetic polarity was given. In the case of the rotatable permanent magnet, the binding means can be vibrated in accordance with the frequency of polarity variation applied to the binding means by the rotation of the permanent magnet. In the case of the electromagnet, by ON-OFF switching of the electromagnet at a constant frequency, the binding means can be vibrated in accordance with the frequency of ON-OFF switching.

The vibration inducing means capable of inducing vibration by optical means may be preferably, for example, a material whose conformational structure can be varied in accordance with the presence/absence of exposure or the change of wavelength of the exposure light. If the binding means were bound to such a material, the binding means can be vibrated in accordance with the ON-OFF switching frequency of the exposure or the frequency of switching the type of exposure light.

The vibration inducing means capable of inducing vibration by mechanical stimulation may be preferably, for example, a piezoelectric element, a stirring apparatus, or a shaker. In these cases, the binding means can be vibrated in accordance with their vibration frequency.

The frequency of the vibration induced by the vibration inducing means is not particularly restricted, and may be selected suitably depending upon the intended application, and is preferably, for example, 1 to 10 MHz, and more preferably 1 to 10 kHz.

The amplitude of the vibration induced by the vibration inducing means is not particularly restricted, and may be selected suitably depending upon the intended application, and is preferably, for example, 0.1 nm to 10 µm, and more preferably 1 nm to 100 nm.

The binding means are not particularly restricted as long as they are capable of resonating with the vibration induced by the vibration inducing means and capable of binding or interacting with a target biopolymer, and may be suitably selected from known means depending upon the intended application, and include binding means that preferably comprise a responding part capable of resonating with the vibration applied by the vibration inducing means, and a binding part capable of binding or interacting with the target biopolymer.

Shape, structure, size, or material of the binding means is not particularly restricted, and may be suitably selected depending upon the intended application.

The responding part preferably has flexibility. In this case, it is advantageous that the responding part can be vibrated efficiently. Also, the responding part preferably has electrical conductance.

The responding part which has the flexibility and the electrical conductance may be, for example, a carbon nanotube, a silicon thin film or a quartz oscillator. Among them, a carbon nanotube is particularly preferable in view of durability, control of vibration, and ease of manufacturing, and the like.

The above-mentioned carbon nanotube is not particularly restricted, and may be selected suitably depending upon the intended application. For example, its shape may be linear (having a generally linear axis), or may be curvilinear (having a curvilinear axis). However, it is preferably linear in view of control of the vibration. The structure may be single wall structure or multi-wall structure, but is preferably single wall structure in view of good flexibility. The size is preferably about 0.4 to 10 nm in diameter.

The method of manufacturing the above-mentioned carbon nanotube is not particularly restricted, and the carbon nanotube may be manufactured by any known method. A manufacturing method such as a chemical vapor deposition (CVD) under a DC electric field, or a chemical vapor deposition (CVD) using a structure having a generally linear cavity under a DC electric field is preferable in view of manufacturing the linear carbon nanotube.

The above-mentioned structure which has a generally linear cavity is not particularly restricted, and may be selected suitably depending upon the intended application. For example, alumina that has been subjected to anodic oxidation processing may be advantageously used.

When the above-mentioned chemical vapor deposition (CVD) method is used to manufacture the carbon nanotube, a catalyst layer is used to grow the carbon nanotube on the catalyst layer. In this case, as the material for the catalyst layer, a transition metal, such iron, nickel, or cobalt, may be used advantageously.

When the carbon nanotube is manufactured by the above-mentioned chemical vapor deposition (CVD) method, gas raw material is not particularly restricted, and may be selected suitably depending upon the intended application, and methane gas may be used advantageously. The chemical deposition method is not particularly restricted, and may be selected suitably depending upon the intended application. For example, a thermal CVD, a plasma enhanced CVD, or the like, may be advantageously used. The apparatus for carrying out the chemical vapor deposition method is not particularly restricted, and any known apparatus may be used. Conditions for the chemical vapor deposition is not particularly restricted, and may be suitably selected depending upon the intended application, and for example, a condition such as a substrate temperature of 500° C. or higher may be used.

The silicon thin film, etc., can be manufactured, for example, by the manufacturing process for micro-machines.

The binding part is not particularly restricted, and may be suitably selected depending upon the intended application. It is preferably at least one of the material, antibody, and fragment of antibody that is capable of binding or interacting with a target biopolymer under physiological conditions.

The target biopolymer is not particularly restricted, and may be suitably selected depending upon the intended application, and may be, for example, a nucleic acid, a lipid, a sugar, a protein or the like.

The above-mentioned material is not particularly restricted, and may be suitably selected depending upon the intended application, and may be, for example, a nucleic acid, a lipid, a sugar, a material as a substrate of an enzyme, an allosteric regulating agent, an agonist, an antagonist to a receptor protein, or their derivatives, a protein that interacts with the target biopolymer in the body, a protein that forms a composite material with the target biopolymer in the body, etc. The material may be obtained by suitable synthesis, or by isolation and refinement.

The antibody is not particularly restricted, and may be suitably selected depending upon the intended application. For example, it may be an anti-target biopolymer IgG antibody, an anti-target biopolymer IgA antibody, an anti-target biopolymer IgM antibody, an anti-target biopolymer IgD antibody, or an anti-target biopolymer IgE antibody. Among them, it is preferably an anti-target biopolymer IgG antibody. The antibody may be either a monoclonal antibody or a polyclonal antibody, but is preferably a monoclonal antibody. It can be obtained by suitable known method.

The fragment of antibody is not particularly restricted, and may be suitably selected depending upon the intended application. For example, it may be a Fab fragment of the above-mentioned antibody, a fragment including a part or all of the variable region of the antibody, or the like. The fragment of antibody can be obtained by suitable known method, such as by processing of the antibody with an enzyme, by using a gene recombination of the lymphocyte that produces the antibody, etc.

The binding part may be used in only one type alone or in combination of two or more types. When plural target biopolymers are to be quantified at a time, a combination of two or more types is preferably used as the binding part, and more preferably, plural fractions of the binding part are present with each fraction of the binding part being capable of binding or interacting with a different target biopolymer.

Bonding of the responding part and the binding part is not particularly restricted, and may be suitably selected depending upon the intended application. For example, it may be a chemical bond or physical adsorption, and it is preferably a chemical bond in view of stability, etc., and more preferably a covalent bond or a coordinate bond.

When the responding part is a carbon nanotube, for example, after the carbon nanotube is processed under oxygen plasma atmosphere, an aqueous solution of the material which is to form the binding part (for example, the antibody) may be sprayed to the carbon nanotube to freeze the aqueous solution by adiabatic expansion and to form the dried body of the material which is to form the binding part (for example, the antibody), supplying the dried body to the carbon nanotube and causing the dried body to be bound to the tip of the carbon nanotube. The aqueous solution is not particularly restricted, and may be suitably selected depending upon the intended application. For example, a pH buffer solution of ammonium carbonate (pH 7) may be advantageously used.

The carbon nanotube has a tube structure of continued aromatic rings of six carbon atoms and contains a five-membered ring at the tip. When the carbon nanotubes are processed under the oxygen plasma atmosphere, or when the carbon nanotubes are processed in a milling process using an argon plasma, or the like, the five-membered ring is opened and a dangling bond is produced. If the material which is to form the binding part is sprayed onto it and reacted, the material which is to form the binding part efficiently forms a chemical bond with the dangling bond. By this method, the desired material can be easily, quickly and efficiently bonded chemically to the tip of the carbon nanotubes.

The detection means are not particularly restricted as long as they can detect whether or not the binding means have bound or interacted with the target biopolymer, and may be selected suitably depending upon the intended application from known means. For example, means for detecting presence/absence of electrical conduction, or means for detecting change of vibration as an image information, may be used. These may be used alone or in combination of two or more of them.

The detection means for detecting the presence/absence of electrical conduction may advantageously comprise, for example, a measuring part which detects the presence/absence of electrical conduction, the measuring part detecting the presence of electrical conduction, and thereby detecting that the binding part has bound or interacted with the target biopolymer.

The detection means for detecting the change of vibration as an image information may advantageously comprise, for example, a measuring part which takes photographs of vibration state of the binding part to detect the amplitude change and thereby the change of vibration of the binding part, the measuring part detecting the change of amplitude, and thereby detecting that the binding part has bound or interacted with the target biopolymer.

The detected change of vibration may be change of natural vibration, change of amplitude, or change of node position of a standing wave, and is preferably change of natural vibration in view of detecting change of resonance state of the binding part.

The detection means preferably comprise, in addition to the measuring part, a data processing part which calculates the amount of the target biopolymer in the sample based on the detection result detected by the measuring part and the dissociation constant of the target biopolymer and the binding part, and a data displaying part capable of displaying the detected result. A known computer may be used as the data processing part and the data displaying part.

The biopolymer detection device according to the present invention can be used, for example, with the binding part disposed in the sample fluid, and can be used for quantifying various proteins, diagnosis of diseases, etc. It can be particularly advantageously used in the biopolymer detection method of the present invention to be described later, and in the disease diagnosis apparatus of the present invention.

The sample fluid is not particularly restricted, and may be suitably selected depending upon the intended application, and may be, for example, body fluid such as blood, lymphatic fluid, saliva, etc., digested matter, excreted fluid such as urine, reaction fluid, purified solution, waste liquid, or a dilution thereof.

The disease is not particularly restricted, and may be suitably selected depending upon the intended application. It is preferably a disease which is caused by decrease or increase of at least one protein from the required amount in a body reaction involving a plurality of proteins, for example, diabetes, hypertension, hyperlipidemia, cancer, or another disease having multiple causes.

The detection sensitivity of the biopolymer detection device according to the present invention may vary depending upon the molecular weight of the target biopolymer to which the binding means bind, and may also vary with the binding constant of the target biopolymer with the binding means. The detection sensitivity can be increased, for example, by arranging different binding means with different binding constants on plural arrays, and the area can be thereby broadened.

The biopolymer detection method according to the present invention comprises a vibration inducing step of inducing vibration in the binding means capable of binding or interacting with the target biopolymer, and a detection step of detecting change in the vibration of the binding means when the binding means bind with the target biopolymer, and further comprises other steps suitably selected as required.

The detection step may be advantageously carried out by above-mentioned detection means. The biopolymer detection method can be advantageously carried out using the biopolymer detection device of the present invention.

The biopolymer detection method can be used, for example, with the binding means disposed in the sample fluid, and can be used advantageously for quantifying various proteins, diagnosis of diseases, etc.

The carbon nanotube structure according to the present invention comprises a binding part capable of binding or interacting with the target biopolymer at the tip of the carbon nanotube, and further comprises other parts as required. Details of the carbon nanotube are as has been described before.

The carbon nanotube structure is manufactured by reacting and bonding the material which is to form the binding part with the dangling bond at the tip of the carbon nanotube produced by processing the carbon nanotube.

Bonding between the carbon nanotube and the binding part is not particularly restricted, and may be suitably selected depending upon the intended application. It may be, for example, either chemical bond or physical adsorption, and is preferably chemical bond in view of stability etc., and more preferably covalent bond or coordinate bond.

The method of the bonding is not particularly restricted, and may be suitably selected depending upon the intended application. For example, after the carbon nanotube is processed, an aqueous solution of the material which is to form the binding part (for example, the antibody) may be sprayed onto the carbon nanotube to freeze the aqueous solution by adiabatic expansion and to produce the dried body of the material which is to form the binding part (for example, the antibody), supplying the dried body to the carbon nanotube and causing the dried body to be bound to the tip of the carbon nanotube. The carbon nanotube has a tube structure of continued aromatic rings of six carbon atoms and contains a five-membered ring at the tip. When the carbon nanotube is processed under an oxygen plasma atmosphere, or when the carbon nanotubes are processed in a milling process using an argon plasma, or the like, the five-membered ring is opened and a dangling bond is produced. If the material which is to form the binding part is sprayed onto it and reacted, the material which is to form the binding part efficiently forms a chemical bond with the dangling bond.

The carbon nanotube structure of the present invention can be used in various applications, and can be used advantageously used in the biopolymer detection apparatus of the present invention, or as the binding means in the biopolymer detection method, or in the disease diagnosis apparatus as described below.

The disease diagnosis apparatus of the present invention comprises above-mentioned biopolymer detection device, and further comprises other devices suitably selected as required.

The disease diagnosis apparatus of the present invention may be designed such that the target biopolymer as a cause of a disease or a marker may be detected alone or may be designed such that two or more biopolymers may be detected.

In the former case, the binding part of the binding means in the biopolymer detection device needs to be capable of binding to only one specific type of the target biopolymer, and is preferably designed to be a monoclonal antibody or a polyclonal antibody for the one specific type of the target biopolymer.

In the latter case, the binding part of the binding means in the biopolymer detection device needs to be capable of binding to two or more specific types of the target biopolymers. For example, the binding part may be designed such that it is divided into types (number) of target biopolymers to be quantified, each binding part being capable of binding or interacting with a different target biopolymer. Or, the biopolymer detection device may be used as a quantifying unit, and be designed such that the biopolymer detection devices is provided in types (number) of the two or more specific target biopolymer, each binding part being capable of binding or interacting with different target biopolymer. Each binding part is preferably designed to be a monoclonal antibody or a polyclonal antibody for the one specific type of the target biopolymer.

The disease diagnosis apparatus according to the present invention can be particularly advantageously used to diagnose the presence/absence of a disease that is caused by decrease or increase from the required amount of at least one protein in a body reaction involving a plurality of proteins, for example, to diagnose diabetes, hypertension, hyperlipidemia, cancer, or another disease having multiple causes.

The sample fluid to be measured by the disease diagnosis apparatus of the present invention is not particularly restricted, and may be selected suitably depending upon the intended application, and may be, for example, body fluid such as blood, lymphatic fluid, saliva, etc., digested matter, excreted fluid such as urine, reaction fluid, purified solution, waste liquid, or a dilution thereof.

With the biopolymer detection device or the disease diagnosis apparatus according to the present invention as described above, the binding part, for example, an antibody or the like, which binds or interacts with the target biopolymer, may be disposed in an array, and the amount of the target biopolymer (a protein or the like) that is present alone in the sample, or the amount of a plurality of target biopolymers (proteins or the like) that exist in the sample, may be comprehensively detected and determined based on the correspondence between change in vibration which is produced when the binding part is bound with the target biopolymer and the position of the binding part (position in the array). Thus, the biopolymer detection device or the disease diagnosis apparatus of the present invention can be advantageously used to function as a protein chip.

With the biopolymer detection device or the disease diagnosis apparatus according to the present invention, diagnosis of diabetes, for example, can be carried out more extensively than before. The diabetes is caused as a result of decrease or increase of a part or all of a series of proteins from an insulin receptor to a glycogenolysis enzyme which are involved in an interacting network when hepatic cells switch the glycogen metabolism in accordance with the insulin reception state. By using the biopolymer detection device or the disease diagnosis apparatus, population of the series of proteins as described above can be grasped, and the protein responsible for the diabetes can be clarified. Consequently, instead of diagnosing the diabetes broadly based solely on the manifested symptoms as before, the protein responsible to the malfunction or the anomaly can be reliably detected and more suitable therapy becomes possible based on detailed and extensive diagnosis.

EXAMPLES

Next, the present invention will be described further with respect to examples thereof. It is to be understood that the present invention is by no means limited by these examples.

Example 1

An example is described below in which carbon nanotubes were grown on a silicon substrate following the steps described with reference to FIGS. 1A to 1D.

First, a 50 nm thick $SiO_2$ film was formed by a plasma enhanced CVD on a silicon substrate. Then, Co ions were implanted through the $SiO_2$ film with implantation energy of 65 keV in a dose not less than $1\times10^{16}$ ions/cm$^2$. Next, a resist pattern was formed on the $SiO_2$ film, and $SF_4$ dry etching was performed on the $SiO_2$ film using the resist pattern as a mask to form an opening of 0.1 to 0.5 μm in diameter for growing carbon nanotubes. After the resist pattern was removed, plasma enhanced CVD was performed at 650° C. using methane gas (acetylene gas may be used instead) and hydrogen gas at reduced pressure of about 1.33 kPa (about 10 Torr) while a DC electric field was applied in a direction perpendicular to the substrate surface to thereby grow carbon nanotubes of 50 nm in the opening.

Example 2

Next, an example is described below in which carbon nanotubes were grown on a silicon substrate following the steps described with reference to FIGS. 2A to 2D.

A 100 nm thick $SiO_2$ film was formed by a plasma enhanced CVD on a silicon substrate, and a resist pattern was formed thereon. Using this resist pattern as a mask, the underlying $SiO_2$ film was etched to midway, by controlling the duration of etching, to form a hole (recess) of 0.1 to 0.5 μm in diameter and 50 nm in depth for growing carbon nanotubes. After the resist pattern was removed, Co ions were implanted with implantation energy of 65 keV in a dose not less than $1\times10^{16}$ ions/cm$^2$. Then, anisotropic etching was performed on the $SiO_2$ film using $SF_4$ dry etching to dig into the $SiO_2$ film in the hole for about 50 nm in vertical direction and to thereby expose the silicon substrate surface, while Co ions remaining in the $SiO_2$ film in other region were removed. Then, carbon nanotubes were grown on the exposed silicon substrate surface in the same conditions as in Example 1.

Example 3

In this example, as shown in FIG. 3, fullerene chemically modified with a catalyst metal was used as seed material for growing carbon nanotubes by a plasma enhanced CVD method.

First, fullerene was dispersed in water, and Ni ions and surface active agent (cyclodextrin) were added to the solution to chemically modify the fullerene with Ni.

Next, a solution of fullerene chemically modified with Ni was coated to a Si substrate (length 10 mm×width 10 mm×thickness 0.5 mm), and by patterning in a lithography method, fullerene chemically modified with Ni was disposed at optional position on the substrate to grow carbon nanotubes by a plasma enhanced CVD method.

Figure 4:
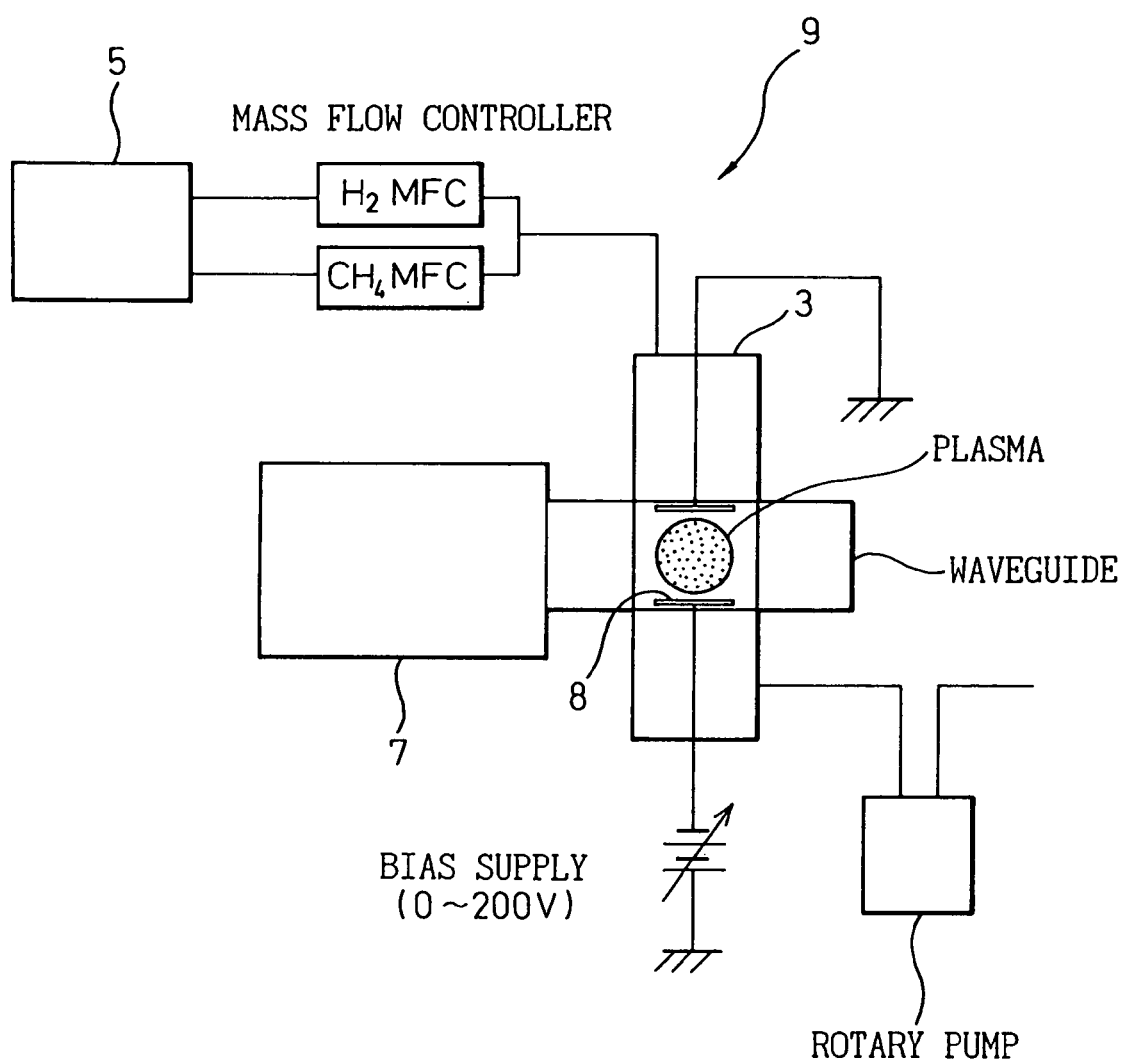
FIG. 4 is a schematic view showing an example of the plasma enhanced CVD apparatus used in example 3.

The plasma enhanced CVD method was performed using a plasma enhanced CVD apparatus 9 as shown in FIG. 4, including a cylinder box 5 and a microwave power source 7 of 2.45 GHz as the excitation source. The substrate 8 was disposed in the vacuum chamber 3, and growth of carbon nanotubes was performed under pressure of 2 Torr, $H_2$ mass flow/$CH_4$ mass flow=80 sccm/20 sccm, and with DC bias of 160 V applied to the substrate 8, for 5 to 30 minutes.

Observation of the growth state of the obtained carbon nanotubes with a scanning type electron microscope (SEM) revealed that, as shown in FIG. 3, single wall carbon nanotubes were grown in uniform diameter (3 nm) in a direction perpendicular to the substrate corresponding to the positions of fullerene chemically modified with Ni disposed on the substrate. The fullerene chemically modified with Ni remained at the tip of the carbon nanotubes (growth at the tip).

Comparative Example 1

Figure 5:
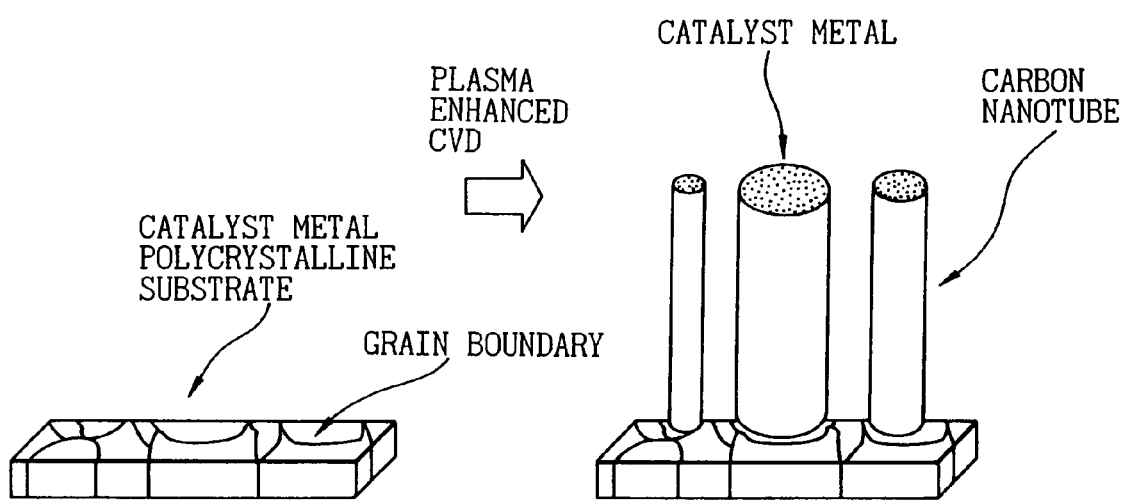
FIG. 5 is a schematic explanatory view showing a conventional method of manufacturing carbon nanotubes according to comparative example 1.

Here, carbon nanotubes were grown by conventional manufacturing method as shown in FIG. 5. In this manufacturing method, carbon nanotubes were grown by a plasma enhanced CVD method in the same manner as in Example 3 except that Ni polycrystal substrate was used as the substrate. Conditions for the plasma enhanced CVD method were same as in Example 3.

The growth state of the obtained carbon nanotubes was observed with an SEM and it was found that, as shown in FIG. 5, non-uniform single wall carbon nanotubes with different diameter and height corresponding to the size of crystal grain boundaries of the Ni polycrystal substrate were grown in a direction perpendicular to the substrate.

Example 4

In this example, as shown in FIG. 6, the diameter and number of walls of the grown carbon nanotubes were controlled by controlling the film thickness of the catalyst metal coated on the fullerene.

As shown in FIG. 6A, Ni was coated to the fullerene by sputtering to film thickness of 3 nm and was designated as fullerene A.

With this fullerene A, a solution of fullerene having Ni coated thereon was coated to a Si substrate (length 10 mm×width 10 mm×thickness 0.5 mm), and by patterning in a lithography method, fullerene A was disposed at optional positions on the substrate. The substrate having fullerene A disposed thereon was used to grow carbon nanotubes by a plasma enhanced CVD method. Conditions for the plasma enhanced CVD method were same as in Example 3.

The growth state of the obtained carbon nanotubes was observed with SEM, and it was found that, as shown in FIG. 6A, single wall carbon nanotubes were selectively grown in uniform diameter (3 nm) in a direction perpendicular to the substrate corresponding to the position of fullerene having Ni coated thereon disposed on the substrate. The fullerene A having Ni coated thereon remained at the tip of the carbon nanotubes (growth at the tip).

As shown in FIG. 6B, Ni was coated to the fullerene by sputtering to film thickness of 20 nm and this was designated as fullerene B.

With this fullerene B, a solution of fullerene having Ni coated thereon was coated to a Si substrate (length 10 mm×width 10 mm×thickness 0.5 mm), and by patterning using a lithography method, fullerene B was disposed at optional positions on the substrate. The substrate having fullerene B disposed thereon was used to grow carbon nanotubes by a plasma enhanced CVD method. Conditions for the plasma enhanced CVD method were same as in Example 3.

Figure 10:
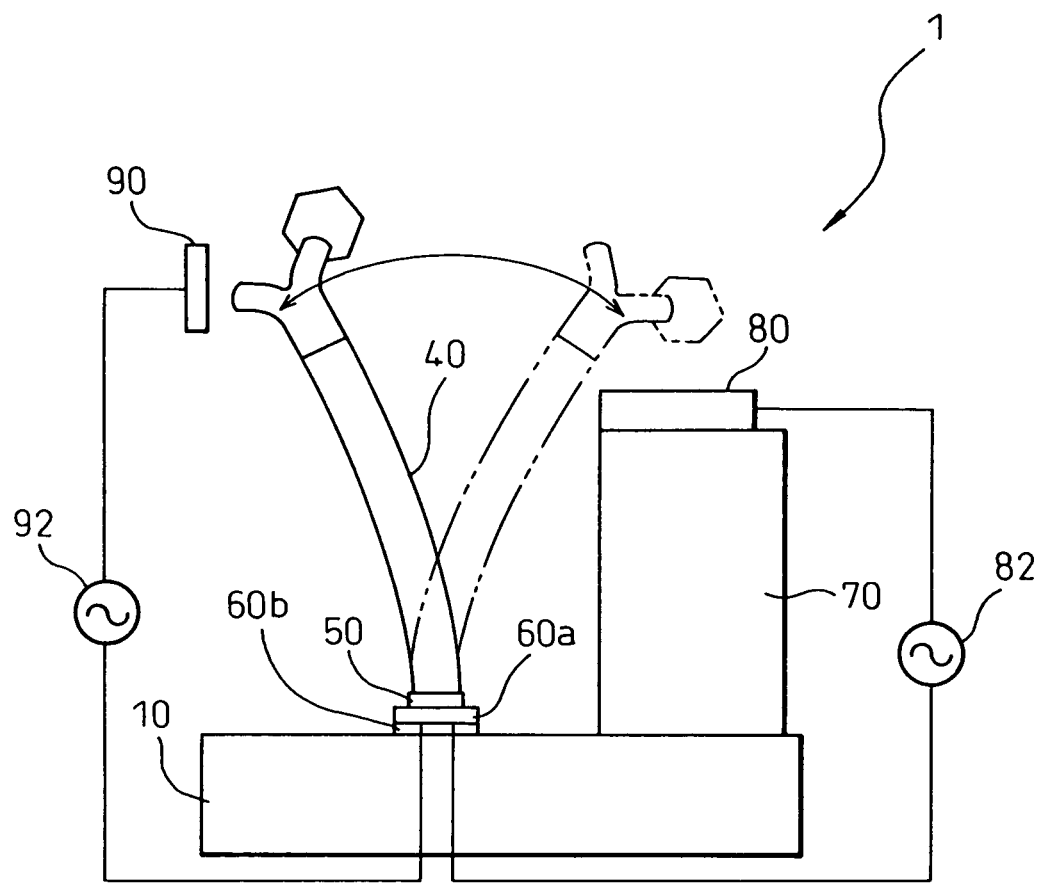
FIG. 10 is a schematic explanatory view showing an example of the detection of the biopolymer detection apparatus in FIG. 8.

The growth state of the obtained carbon nanotubes was observed with SEM, and it was found that, as shown in FIG. 6B, 10-wall carbon nanotubes were selectively grown in uniform diameter (20 nm) in a direction perpendicular to the substrate corresponding to the position of fullerene B having Ni coated thereon disposed on the substrate. The fullerene B having Ni coated thereon remained at the tip of the carbon nanotubes (growth at the tip).

From the result described above, it was confirmed that the diameter of the carbon nanotubes grown with the fullerene having a catalyst metal coated thereon as seed material can be controlled by controlling the thickness of the catalyst metal layer coated on the fullerene (that is, diameter of fullerene). It was also confirmed that, by increasing the thickness of the catalyst metal layer, multi-wall carbon nanotubes ranging from single wall to two or more walls can be obtained, and that number of walls of the carbon nanotubes grown with the fullerene having the catalyst metal coated thereon as seed material can be controlled by controlling the thickness of the catalyst metal layer coated on the fullerene (that is, diameter of fullerene).

Example 5

In this example, by the method as shown in FIG. 7, carbon nanotubes were selectively grown by a thermal CVD method using fullerene chemically modified with a catalyst metal as seed material.

Fullerene was chemically modified with Ni in the same manner as in Example 3, and the fullerene chemically modified with Ni was periodically disposed by a lithography method on a Si substrate (not shown: length 10 mm×width 10 mm×thickness 0.5 mm) as shown in FIG. 7, and carbon nanotubes were selectively grown by a thermal CVD method.

The thermal CVD method was performed using a commonly used thermal CVD apparatus at temperature of 800° C., pressure of 2 Torr, and $H_2$ mass flow/$CH_4$ mass flow=80 sccm/20 sccm, with DC bias of 160 V applied to the substrate, to grow carbon nanotubes for 5 to 30 minutes.

The growth state of the obtained carbon nanotubes was observed with SEM, and it was found that, as shown in FIG. 7, single wall carbon nanotubes were grown in uniform diameter (3 nm) in a direction perpendicular to the substrate corresponding to the position of the fullerene chemically modified with Ni disposed periodically on the substrate. In the thermal CVD method, the fullerene chemically modified with Ni remained at the base of the carbon nanotubes (growth at the base).

It was found from the result of this example, that, in accordance with the method of manufacturing carbon nanotubes of the present invention, carbon nanotubes having uniform diameter and/or number of walls and arranged at desired position on the substrate in high precision can be obtained.

Example 6

Figure 8:
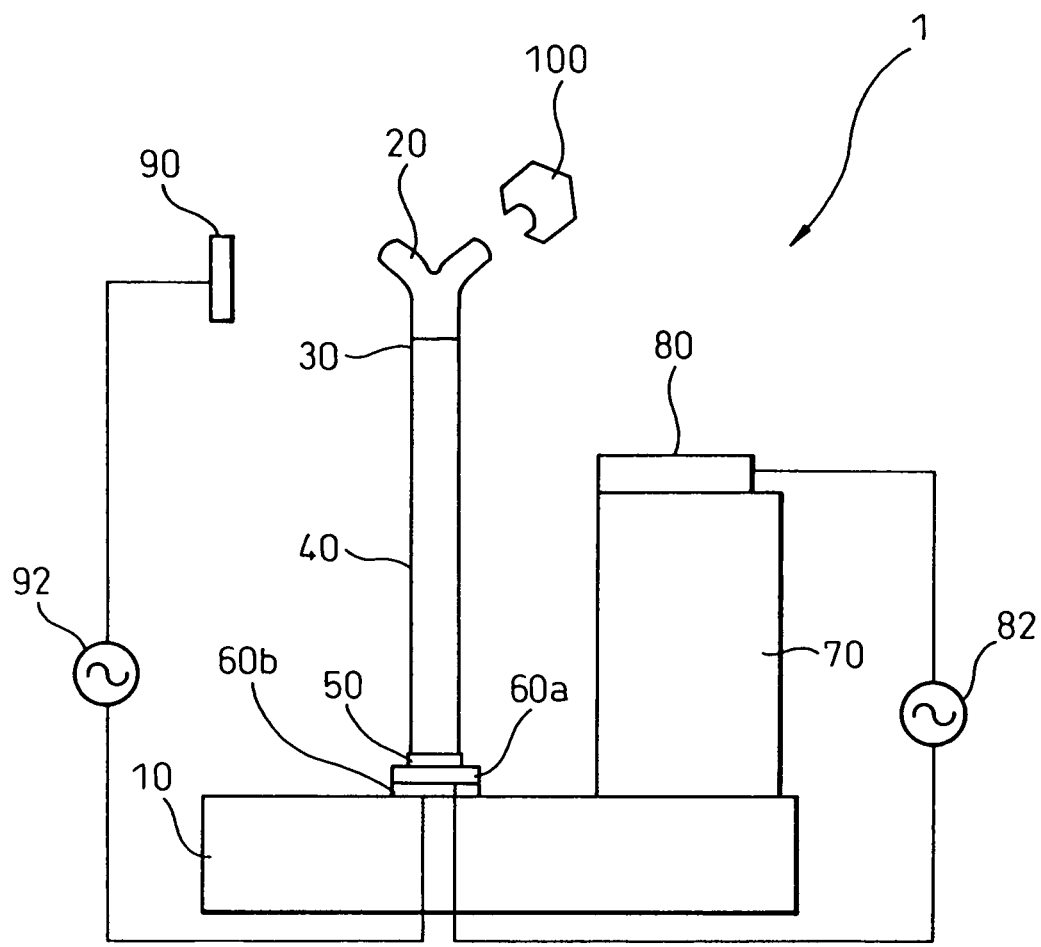
FIG. 8 is a schematic explanatory view showing an example of a biopolymer detection method according to the present invention using a biopolymer detection apparatus of the present invention.

Next, the biopolymer detection apparatus in this example will be described with reference to FIGS. 8 to 10. As shown in FIG. 8, this biopolymer detection apparatus 1 comprises a silicon substrate 10, anti-CEA antibody Fab fragment 20, a carbon nanotube 40, a base electrode 60a, a vibration inducing electrode 80, an AC power source 82, a base electrode 60b, a vibration detection electrode 90 and an ammeter 92.

The silicon substrate 10 is a support for fixing various members of the biopolymer detection apparatus. Although a silicon substrate is used in this example, a substrate formed of another material may be used as a support.

On the silicon substrate 10, a base electrode 60b and a base electrode 60a are laminated in this order. The base electrode 60b and the base electrode 60a were formed of titanium in this example. A catalyst layer 50 is provided on the base electrode 60a. In this example, the catalyst layer 50 was formed of iron, but nickel, cobalt or the like may be used. Carbon nanotubes were formed on the catalyst layer 50 as follows. With a DC voltage applied in a direction perpendicular to the silicon substrate 10, temperature of the silicon substrate 10 was raised to 500° C. or higher, and methane gas was supplied as a raw material gas and generally linear carbon nanotube 40 was grown by a thermal CVD method on the catalyst layer 50 in a direction generally perpendicular to the silicon substrate 10. In this example, the carbon nanotube 40 functions as the responding part.

Then, anti-CEA antibody fragment Fab was bound to the tip of the carbon nanotube 40 as follows. The carbon nanotube was ashing-processed with oxygen plasma to open the five-membered ring at the tip of the carbon nanotube 40 to produce dangling bond 30. The anti-CEA antibody Fab fragment was dissolved in 10 mM ammonium carbonate pH buffer solution (pH 7) and sprayed and introduced into the vacuum system in which the carbon nanotube 40 having the dangling bond 30 was disposed. As a result of adiabatic expansion, moisture froze and sublimated to produce freeze-dry powder of anti-CEA antibody Fab fragment, and the freeze-dry powder of anti-CEA antibody Fab fragment reacted with the dangling bond 30 of the carbon nanotube 40 so as to fix the anti-CEA antibody Fab fragment 20 at the tip of the carbon nanotube 40. In this example, the anti-CEA antibody Fab fragment 20 functions as the binding part, and the anti-CEA antibody Fab fragment 20 together with the carbon nanotube 40 functions as the binding means.

On the silicon substrate 10, a protrusion 70 for placing the vibration inducing electrode is provided near the carbon nanotube 40 and the vibration inducing electrode 80 is disposed on the protrusion 70 for placing the vibration inducing electrode. The vibration inducing electrode 80 and the base electrode 60a are conductively connected via the AC power source 82. The AC power source 82 and the vibration inducing electrode 80 and the base electrode 60a conductively connected thereto function as the vibration inducing means. In this example, the vibration inducing electrode 80 is formed of aluminium.

A vibration detection electrode 90 is disposed near the carbon nanotube 40, the vibration detection electrode 90 and the base electrode 60b being conductively connected via an ammeter 92. The ammeter 92 and the vibration detection electrode 90 and the base electrode 60b conductively connected thereto function as the detection means. In this example, the vibration detection electrode 90 is formed of aluminium.

Figure 9:
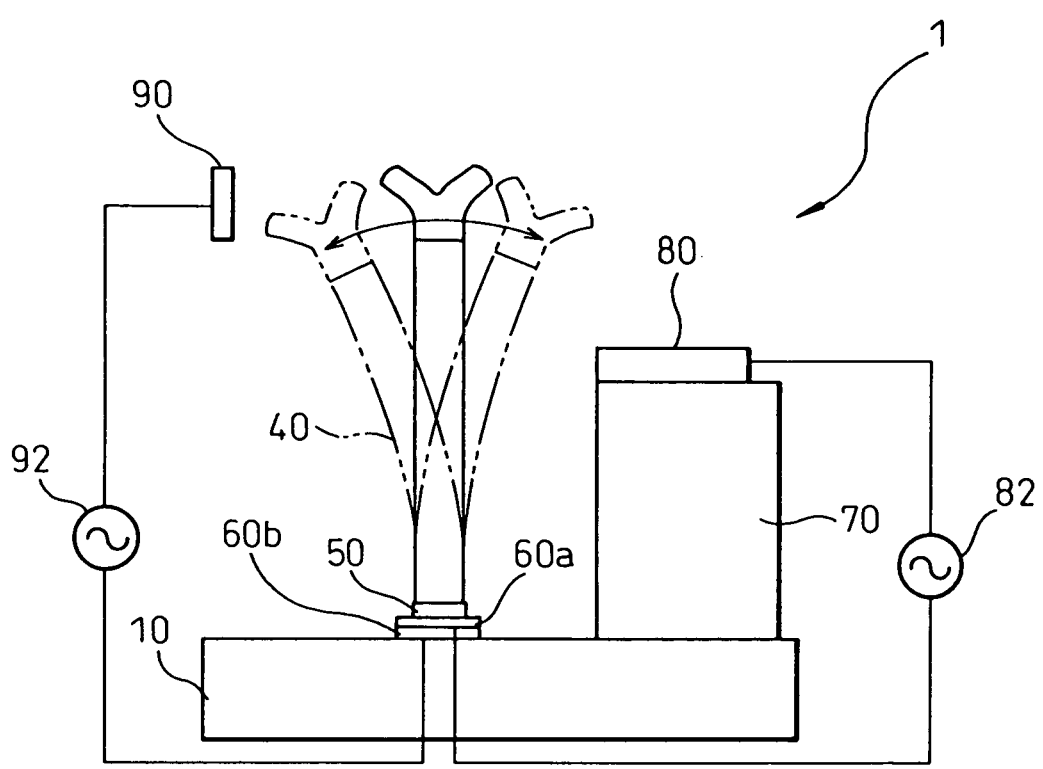
FIG. 9 is a schematic explanatory view showing an example of the operation of the biopolymer detection apparatus in FIG. 8.

In the biopolymer detection device 1 in this example, when an AC voltage was applied from the AC power source 82, the AC voltage was applied between the vibration inducing electrode 80 and the base electrode 60, and the conductive carbon nanotube 40 resonated in accordance with the frequency of the AC electric field, as shown in FIG. 9, so as to move to and from the vibration inducing electrode 80. The anti-CEA antibody Fab fragment 20 bound to the tip of the carbon nanotube 40 also resonated together with the carbon nanotube 40.

In this example, the frequency of the vibration of the resonating carbon nanotube 40 was 1 to 10 MHz, and the amplitude was several nm to several tens of μm.

The anti-CEA antibody Fab fragment 20 fixed to the tip of the carbon nanotube 40 is capable of binding with a tumor marker CEA protein 100 as the target biopolymer via antigen-antibody reaction. Thus, when the anti-CEA antibody Fab fragment 20 was disposed in a sample solution containing the tumor marker CEA protein 100 as the target biopolymer, the anti-CEA antibody Fab fragment 20 bound with the CEA protein 100 via antigen-antibody reaction. In this case, the anti-CEA antibody Fab fragment 20 did and the CEA protein 100 were not bound with each other continuously, but was bound and dissociated with each other in accordance with the dissociation constant of the anti-CEA antibody Fab fragment 20.

The resonating state of the carbon nanotube 40 to move to and from the vibration inducing electrode 80 was measured (monitored) with the ammeter 92 as the intermittent conduction pattern of current flowing between the vibration detection electrode 90 disposed near the carbon nanotube 40 and the base electrode 60b provided at the end portion of the carbon nanotube 40. In this example, an on-off pattern of current passing between the vibration detection electrode 90 and the base electrode 60b was measured (monitored) by applying a 1 volt DC voltage to the electric circuit formed by the vibration detection electrode 90 and the base electrode 60b.

When the anti-CEA antibody Fab fragment 20 was bound with the CEA protein 100, mass at the tip of the carbon nanotube 40 was increased so that the resonant frequency of the carbon nanotube 40 changed and, as shown in FIG. 10, the amplitude of the carbon nanotube was increased and consequently, the intermittent conduction pattern of current flowing between the vibration detection electrode 90 and the base electrode 60b changed. By detecting change in the intermittent conduction pattern of current, presence of CEA protein 100 in the sample could be detected, and further, the amount of CEA protein 100 in the sample could be quantified using the dissociation constant between the amount of the CEA protein 100 in the sample and the anti-CEA antibody Fab fragment 20.

Example 7

Figure 11:
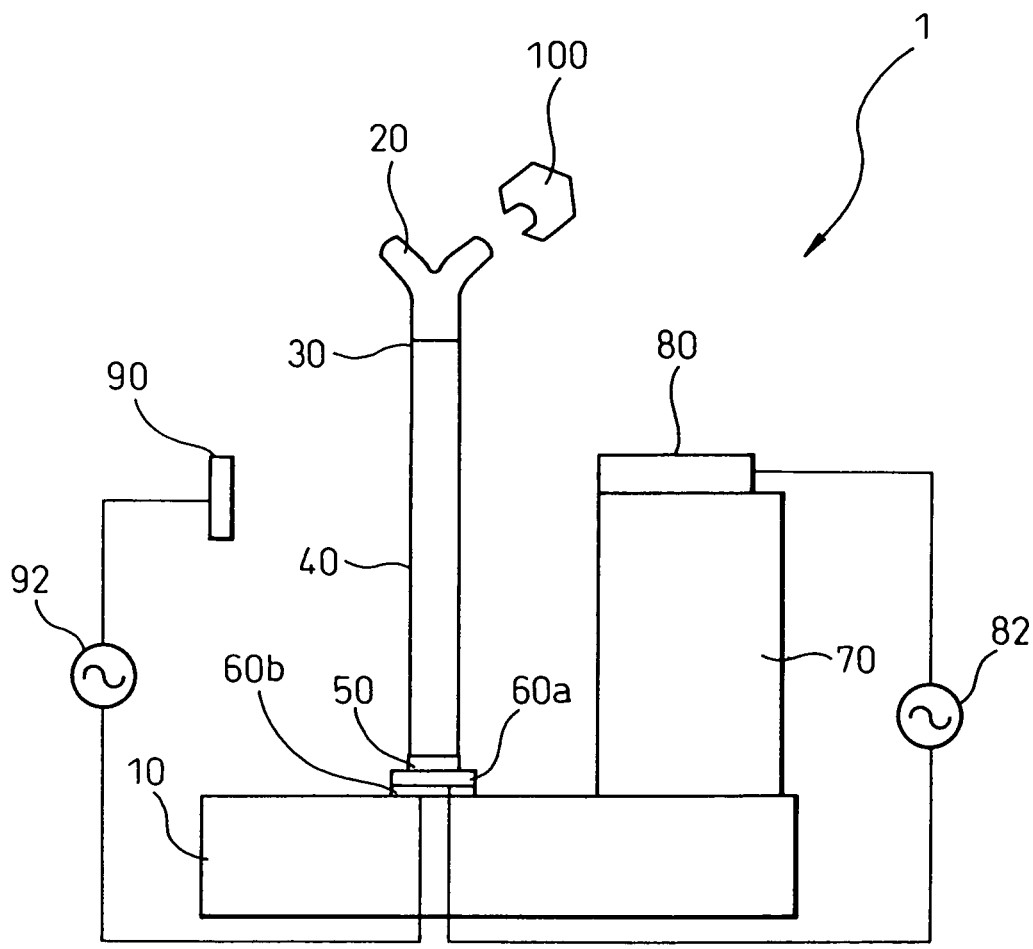
FIG. 11 is a schematic explanatory view showing another example of a biopolymer detection method according to the present invention using a biopolymer detection apparatus of the present invention.
Figure 12:
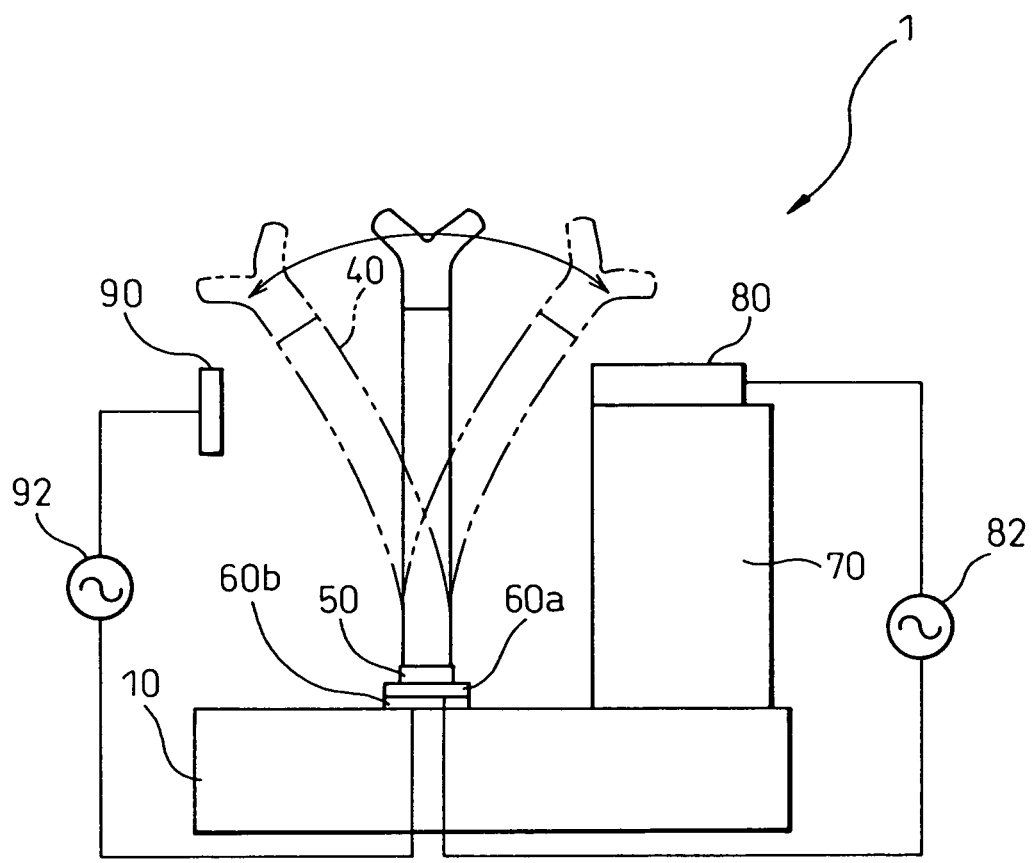
FIG. 12 is a schematic explanatory view showing an example of the operation of the biopolymer detection apparatus in FIG. 11.
Figure 13:
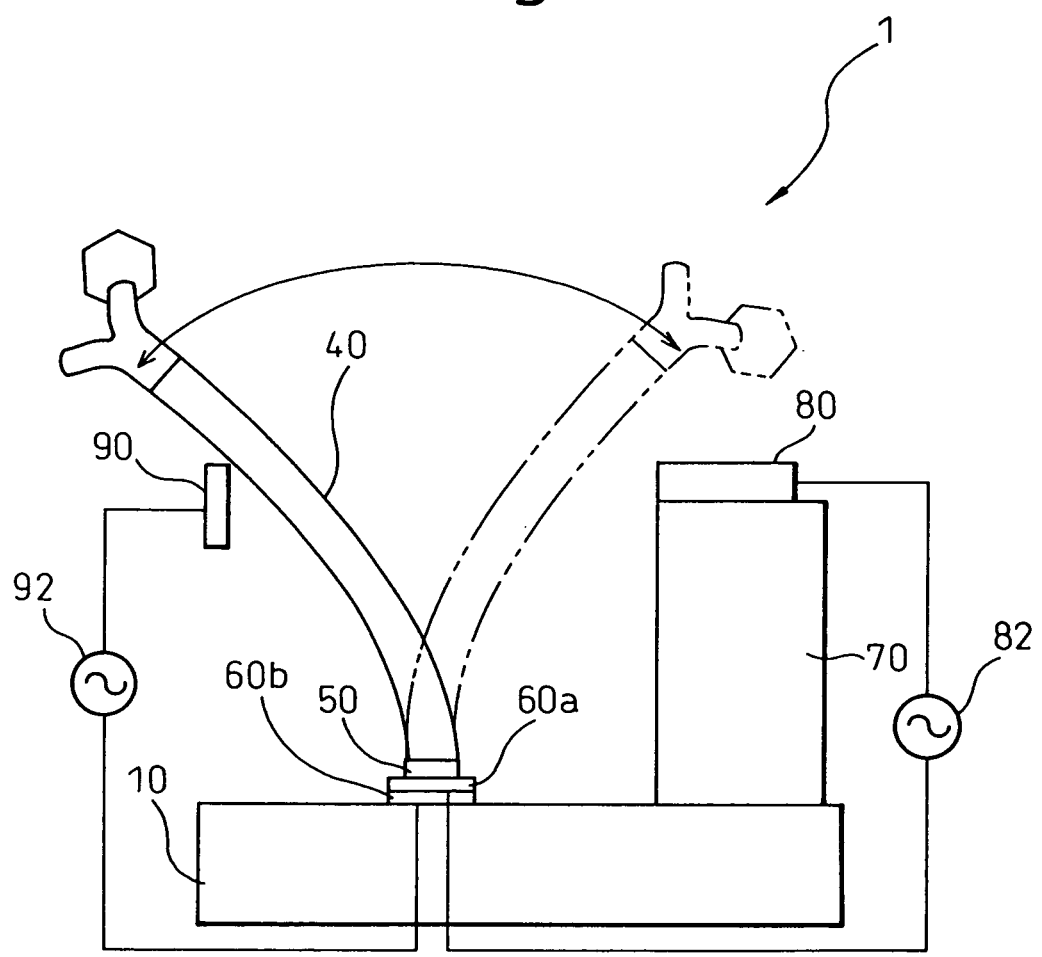
FIG. 13 is a schematic explanatory view showing an example of the detection of the biopolymer detection apparatus in FIG. 11.

A biopolymer detection apparatus in this example will be described below with reference to FIGS. 11 to 13. As shown in FIG. 11, the biopolymer detection apparatus 1 in this example differs from the biopolymer detection apparatus 1 in Example 1 in that the vibration detection electrode 90 is disposed close to the carbon nanotube 40. In the biopolymer detection apparatus 1 in this example, as shown in FIG. 12, before the anti-CEA antibody Fab fragment 20 is bound to the CEA protein 100, the carbon nanotube 40 vibrates in the same manner as in Example 1. When the anti-CEA antibody Fab fragment 20 was bound to the CEA protein 100, as shown in FIG. 13, the carbon nanotube 40 vibrated in larger amplitude so that it came into contact with the vibration detection electrode 90 and current flowed directly between the vibration electrode 90 and the base electrode 60b. The presence of the CEA protein 100 in the sample could be detected by detecting the change in the direct conduction pattern of current, and further, the amount of CEA protein 100 in the sample could be quantified using the dissociation constant between the amount of the CEA protein 100 in the sample and the anti-CEA antibody Fab fragment 20.

Figure 14:
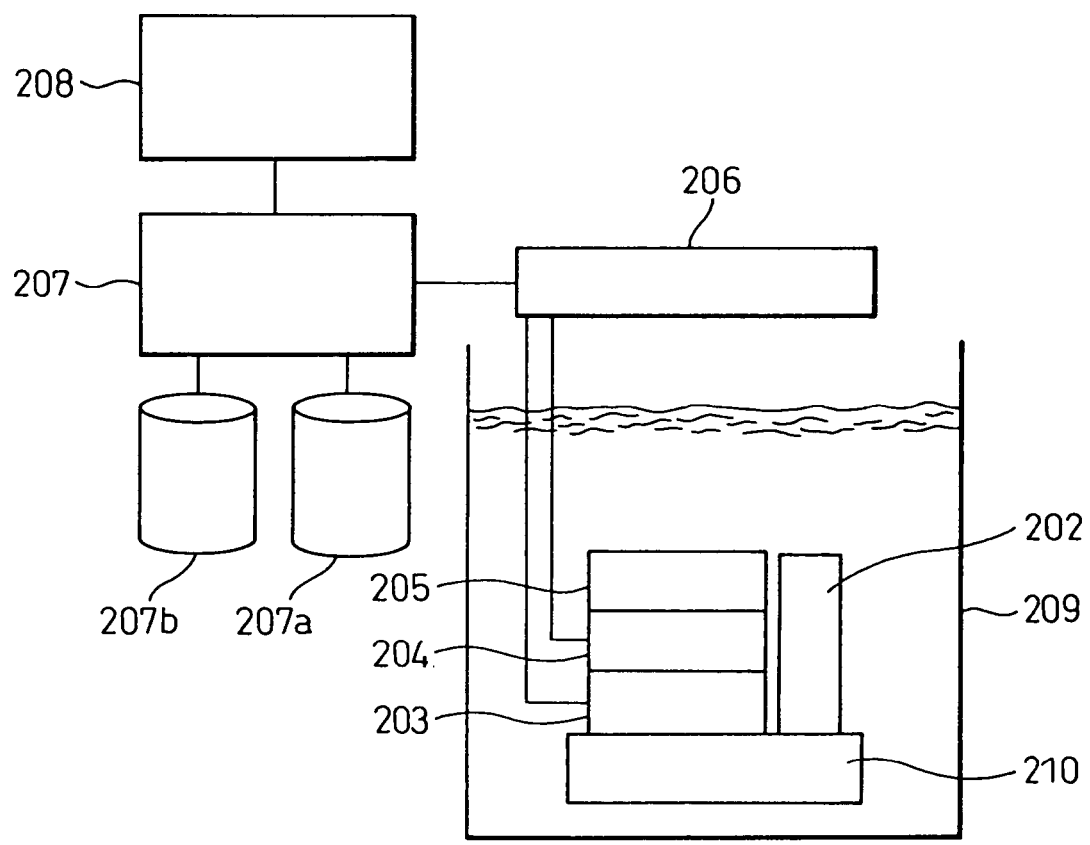
FIG. 14 is a block diagram showing an example of the biopolymer detection apparatus according to the present invention.

The biopolymer detection apparatus 1 in Examples 6 and 7 is shown in the block construction view in FIG. 14. The vibration inducing part 202, detection part 203, responding part 204 and binding part 205 are disposed on the silicon substrate 210. These are disposed in a sample container 209 in which the sample fluid is contained.

The vibration inducing part 202 is composed of a protrusion 70 for placing the vibration inducing electrode, a vibration inducing electrode 80, an AC power source 82 and a base electrode 60a. The detection part 203 is composed of a base electrode 60b, a vibration detection electrode 90 and an ammeter 92. The binding part 205 is composed of anti-CEA antibody Fab fragment 20. A measuring part 206 is connected to the vibration inducing part 202, the detection part 203 and the responding part 204, and it measures (monitors) the change in these currents. The measuring part 206 is connected to a data processing part 207 where the measurement data are checked and calculated against calibration data 207a and array arrangement data 207b, and the amount of the CEA protein 100 is quantified. The results are displayed on the data displaying part 208.

Figure 15:
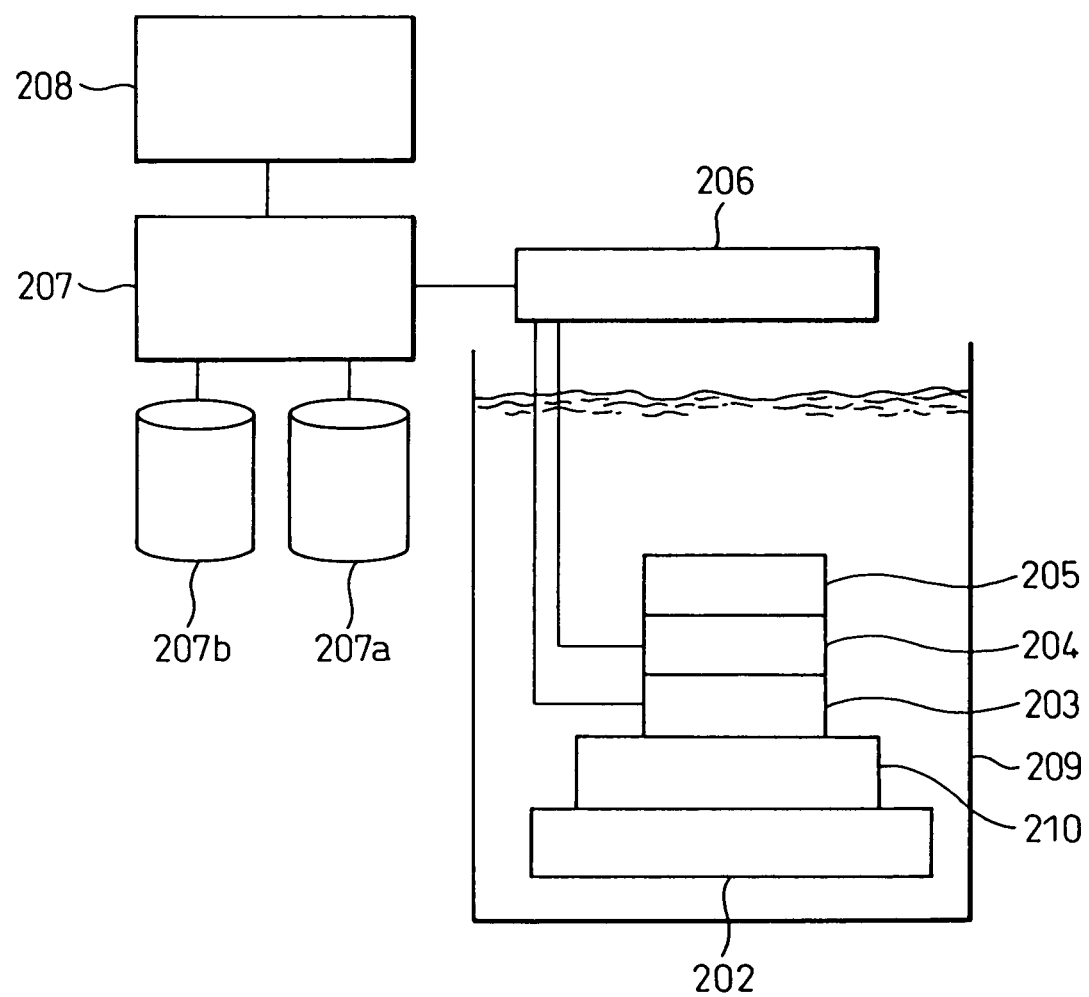
FIG. 15 is a block diagram showing another example of the biopolymer detection apparatus according to the present invention.

A block construction view in FIG. 15 shows a biopolymer detection apparatus which differs from the biopolymer detection apparatus 1 in Examples 6 and 7 in that a piezoelectric element as a vibration inducing part 202 is disposed on the silicon substrate 210 on the side opposite to the detection part 203, responding part 204 and binding part 205. This biopolymer detection apparatus exhibits same operative effect as the biopolymer detection apparatus 1 in Examples 6 and 7.

As has been described above, in accordance with the manufacturing method of the present invention, a catalyst metal which has been hitherto difficult to be formed in microparticles can be fixed and stably provided in nanometer-size in individually independent location on the surface of a substrate. Controllability of the diameter of carbon cylindrical structures such as carbon nanotubes can be thereby remarkably improved, and in addition, a chirality change and the twisting of carbon nanotubes can be suppressed.

In accordance with another manufacturing method of the present invention, carbon nanotubes having controlled diameters and/or number of walls can be manufactured efficiently, and single wall and multi-wall carbon nanotubes having a uniform diameter and/or number of walls and having uniform electrical characteristics is provided by the manufacturing method.

Further, in accordance with the biopolymer detection device of the present invention, the amount of a series of plural proteins that are contained in a sample in close functional relation with each other can be easily, reliably and quickly detected, and diagnosis of a disease or the like can be thereby efficiently carried out. By using this method, a biopolymer detection device and a biopolymer detection method capable of being applied to an array chip technology, and carbon nanotubes used for same, and a disease diagnosis apparatus, can be provided.

What is claimed is:

1. A method of manufacturing carbon cylindrical structures, which uses a chemical vapor deposition (CVD) method to grow carbon cylindrical structures on a substrate, comprising the steps of implanting metal ions to the surface of the substrate, and using the metal ions as a catalyst to grow the carbon cylindrical structures.

2. A method according to claim 1, wherein the implantation of the metal ions is performed through a mask film formed on the surface of the substrate, and after the implantation of the metal ions, an opening is formed in the mask film, carbon cylindrical structures being grown on the substrate surface exposed at the bottom of the opening.

3. A method according to claim 1, wherein the metal ions are selectively implanted to the region of the substrate in which the carbon cylindrical structures are to be grown.

4. A method according to claim 2, wherein the mask film is formed with a recess provided in a portion thereof, and, after the metal ions are implanted through the mask film such that the metal ions reach the substrate surface underlying the recess, the entire mask film is removed in depth direction until the substrate surface containing the metal ions is exposed at the bottom of the recess and, at the same time, the mask film in the portion other than the recess forming portion is removed together with the implanted metal ions contained in the mask film.

5. A method according to claim 2, wherein material for the mask film is a resist material, silicon oxide, silicon nitride, silicon oxynitride, or metal.

6. A method according to claim 1, wherein, after metal ions are implanted, metal ions are diffused to form clusters.

7. A method according to claim 6, wherein the diameter of the cluster is not greater than 20 nm.

8. A method according to claim 1, wherein the metal ions which are introduced to the substrate in advance by ion implantation are exposed at the substrate surface.

9. A method according to claim 1, wherein the metal ions are transition metal ions.

10. A method according to claim 9, wherein the transition metal ions are ions of one or more metal selected from nickel, iron, or cobalt.

11. A method according to claim 1, wherein the chemical vapor deposition is a thermal chemical vapor deposition or a plasma enhanced chemical vapor deposition.

12. A method according to claim 11, wherein the chemical vapor deposition is performed during the application of an electric field.

13. A method according to claim 1, wherein the material for the substrate is a semiconductor or a metal.

14. A method of manufacturing carbon nanotubes, comprising:
    disposing nano-carbon material on a substrate, said nano-carbon material being seed material for growing carbon nano-tubes; and
    selectively growing carbon nano-tubes in a direction generally perpendicular to the substrate;
    wherein the nano-carbon material is chemically modified with a compound containing a catalyst metal; and
    the nano-carbon material is arranged periodically on the substrate.

15. A method of manufacturing carbon nanotubes according to claim 14, wherein the selective growth is performed by a CVD method.

16. A method of manufacturing carbon nanotubes according to claim 15, wherein the CVD method is selected from a plasma enhanced CVD method and a thermal CVD method.

17. A method of manufacturing carbon nanotubes according to claim 14, wherein the nano-carbon material comprises coating with a catalyst metal.

18. A method of manufacturing carbon nanotubes according to claim 14, wherein the catalyst metal is at least one of transition metals and transition metal compounds.

19. A method of manufacturing carbon nanotubes according to claim 17, wherein the catalyst metal is at least one of transition metals and transition metal compounds.

20. A method of manufacturing carbon nanotubes according to claim 18, wherein the transition metal is selected from Fe, Co, and Ni.

21. A method of manufacturing carbon nanotubes according to claim 19, wherein the transition metal is selected from Fe, Co, and Ni.

22. A method of manufacturing carbon nanotubes according to claim 14, wherein the diameter of the carbon nanotubes is controlled by controlling the diameter of the nano-carbon material.

23. A method of manufacturing carbon nanotubes according to claim 14, wherein number of walls of multi-wall carbon nanotubes is controlled by controlling the thickness of the catalyst metal layer of nano-carbon material coated with the catalyst metal.

24. A method of manufacturing carbon nanotubes according to claim 14, wherein the nano-carbon material is fullerene.

25. A method of manufacturing carbon nanotubes according to claim 24, wherein the fullerene is $C_{60}$.

* * * * *